United States Patent
Bolli et al.

(10) Patent No.: US 7,323,465 B2
(45) Date of Patent: Jan. 29, 2008

(54) ALKANSULFONAMIDES AS ENDOTHELIN ANTAGONISTS

(75) Inventors: Martin Bolli, Allschwil (CH);
Christoph Boss, Allschwil (CH);
Martine Clozel, Binningen (CH);
Walter Fischli, Allschwil (CH);
Thomas Weller, Binningen (CH)

(73) Assignee: Actelion Pharmaceuticals Ltd. (CH)

( * ) Notice: Subject to any disclaimer, the term of this patent is extended or adjusted under 35 U.S.C. 154(b) by 462 days.

(21) Appl. No.: 10/500,485

(22) PCT Filed: Dec. 10, 2002

(86) PCT No.: PCT/EP02/13970

§ 371 (c)(1),
(2), (4) Date: Jun. 29, 2004

(87) PCT Pub. No.: WO03/055863

PCT Pub. Date: Jul. 10, 2003

(65) Prior Publication Data
US 2005/0085639 A1    Apr. 21, 2005

(30) Foreign Application Priority Data
Jan. 2, 2002    (WO)    ............. PCT/EP02/00002

(51) Int. Cl.
*C07D 239/47* (2006.01)
*A61K 31/506* (2006.01)

(52) U.S. Cl. ............... 514/235.8; 514/255.05; 514/269; 544/123; 544/296; 544/319

(58) Field of Classification Search ............... 544/123, 544/296, 319; 514/235.8, 255.05, 269
See application file for complete search history.

(56) References Cited

FOREIGN PATENT DOCUMENTS

| | | |
|---|---|---|
| EP | 0743307 | 11/1996 |
| EP | 1191026 | 3/2002 |
| WO | WO98/57938 | * 12/1998 |
| WO | WO0117976 | 3/2001 |

OTHER PUBLICATIONS

Simone, Oncology: Introduction, Cecil Textbook of Medicine, 20th Edition, vol. 1, pp. 1004-1010, 1996.*
Rubanyi et al., Endothelins: Molecular Biology, Biochemistry, Pharmacology, Physiology, and Pathophysiology, Pharmacological Reviews, vol. 46, No. 3, pp. 325-415, 1994.*
Harada, Hironori, et al., "Ethenesulfonamide and Ethanesulfonamide Derivatives, a Novel Class or Orally Active Endothelin-A Receptor Antagonists", Bioorganic & Medicinal Chemistry, 2001, vol. 9, pp. 2955-2968.

* cited by examiner

*Primary Examiner*—Deepak Rao
(74) *Attorney, Agent, or Firm*—Hoxie & Associates LLC

(57) ABSTRACT

The invention relates to novel alkansulfonamides of structure (I), wherein $R^1$ is a lowel alzyl group and the other variables are as defined in the description, and their use as active ingredients in the preparation of pharmaceutical compositions. The invention also concerns related aspects including processes for the preparation of the compounds, pharmaceutical compositions containing one or more of those compounds and especially their use as endothelin receptor antagonists in the treatment and prevention of diseases associated to the endothelin system

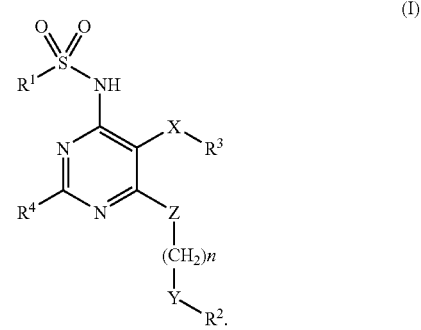

9 Claims, No Drawings

ALKANSULFONAMIDES AS ENDOTHELIN ANTAGONISTS

The present invention relates to novel alkanesulfonamides of the general formula I and their use as active ingredients in the preparation of pharmaceutical compositions. The invention also concerns related aspects including processes for the preparation of the compounds, pharmaceutical compositions containing one or more compounds of the general formula I and especially their use as endothelin receptor antagonists.

Endothelins (ET-1, ET-2, and ET-3) are 21-amino acid peptides produced and active in almost all tissues (Yanagisawa M et al.: Nature (1988) 332:411). Endothelins are potent vasoconstrictors and important mediators of cardiac, renal, endocrine and immune functions (McMillen M A et al.: J Am Coll Surg (1995) 180:621). They participate in bronchoconstriction and regulate neurotransmitter release, activation of inflammatory cells, fibrosis, cell proliferation and cell differentiation (Rubanyi G M et al.: Pharmacol Rev (1994) 46:328).

Two endothelin receptors have been cloned and characterized in mammals ($ET_A$, $ET_B$) (Arai H et al.: Nature (1990) 348:730; Sakurai T et al.: Nature (1990) 348:732). The $ET_A$ receptor is characterized by higher affinity for ET-1 and ET-2 than for ET-3. It is predominant in vascular smooth muscle cells and mediates vasoconstricting and proliferative responses (Ohlstein E H et al.: Drug Dev Res (1993) 29:108). In contrast, the $ET_B$ receptor has equivalent affinity for the three endothelin isopeptides and binds the linear form of endothelin, tetra-ala-endothelin, and sarafotoxin S6C (Ogawa Y et al.: BBRC (1991) 178:248). This receptor is located in the vascular endothelium and smooth muscles, and is also particularly abundant in lung and brain. The $ET_B$ receptor from endothelial cells mediates transient vasodilator responses to ET-1 and ET-3 through the release of nitric oxide and/or prostacyclin whereas the $ET_B$ receptor from smooth muscle cells exerts vasoconstricting actions (Sumner M J et al.: Brit J Pharmacol (1992) 107:858). $ET_A$ and $ET_B$ receptors are highly similar in structure and belong to the superfamily of G-protein coupled receptors.

A pathophysiological role has been suggested for ET-1 in view of its increased plasma and tissue levels in several disease states such as hypertension, pulmonary hypertension, sepsis, atherosclerosis, acute myocardial infarction, congestive heart failure, renal failure, migraine and asthma. As a consequence, endothelin receptor antagonists have been studied extensively as potential therapeutic agents. Endothelin receptor antagonists have demonstrated preclinical and/or clinical efficacy in various diseases such as cerebral vasospasm following subarachnoid hemorrhage, heart failure, pulmonary and systemic hypertension, neurogenic inflammation, renal failure and myocardial infarction.

Today, only one endothelin receptor antagonist (bosentan, Tracleer™) is marketed and several are in clinical trials. However, some of these molecules possess a number of weaknesses such as complex synthesis, low solubility, high molecular weight, poor pharmacokinetics, or safety problems (e.g. liver enzyme increases). Furthermore, the contribution of differing $ET_A$/$ET_B$ receptor blockade to the clinical outcome is not known. Thus, tailoring of the physicochemical and pharmacokinetic properties and the selectivity profile of each antagonist for a given clinical indication is mandatory. So far, no endothelin receptor antagonists with a pyrimidine core structure containing an n-alkanesulfonamide unit attached to the 4-position of the core pyrimidine have been reported [2, 3, 5, 6, 8]. We have discovered a new class of substituted pyrimidines of the general formula I below and found that they allow the specific tailoring described above.

In addition, compounds exhibiting mixed as well as $ET_A$-selective binding profiles have been identified.

The inhibitory activity of the compounds of general formula I on endothelin receptors can be demonstrated using the test procedures described hereinafter:

For the evaluation of the potency and efficacy of the compounds of the general formula I the following tests were used:

1) Inhibition of Endothelin Binding to Membranes from CHO Cells Carrying Human ET Receptors:

For competition binding studies, membranes of CHO cells expressing human recombinant $ET_A$ or $ET_B$ receptors were used. Microsomal membranes from recombinant CHO cells were prepared and the binding assay was carried out as previously described (Breu V., et al, FEBS Left 1993; 334:210).

The assay was performed in 200 uL 50 mM Tris/HCl buffer, pH 7.4, including 25 mM $MnCl_2$, 1 mM EDTA and 0.5% (w/v) BSA in polypropylene microtiter plates. Membranes containing 0.5 ug protein were incubated for 2 h at 20° C. with 8 pM [$^{125}$I]ET-1 (4000 cpm) and increasing concentrations of unlabeled antagonists. Maximum and minimum binding were estimated in samples without and with 100 nM ET-1, respectively. After 2 h, the membranes were filtered on filterplates containing GF/C filters (Unifilterplates from Canberra Packard S.A. Zürich, Switzerland). To each well, 50 uL of scintillation cocktail was added (MicroScint 20, Canberra Packard S.A. Zürich, Switzerland) and the filter plates counted in a microplate counter (TopCount, Canberra Packard S.A. Zürich, Switzerland).

All the test compounds were dissolved, diluted and added in DMSO. The assay was run in the presence of 2.5% DMSO which was found not to interfere significantly with the binding. $IC_{50}$ was calculated as the concentration of antagonist inhibiting 50% of the specific binding of ET-1. For reference compounds, the following $IC_{50}$ values were found: $ET_A$ cells: 0.075 nM (n=8) for ET-1 and 118 nM (n=8) for ET-3; $ET_B$ cells: 0.067 nM (n=8) for ET-1 and 0.092 nM (n=3) for ET-3.

The $IC_{50}$ values obtained with compounds of general formula I are given in Table 1.

TABLE 1

| Compound of Example | $IC_{50}$[nM] | |
|---|---|---|
| | $ET_A$ | $ET_B$ |
| Example 1 | 3.96 | >1000 |
| Example 2 | 5.99 | 989 |
| Example 3 | 38.2 | >1000 |
| Example 4 | 6.34 | >1000 |
| Example 5 | 3.6 | >1000 |
| Example 6 | 17.1 | >1000 |
| Example 7 | 16.3 | 367 |
| Example 8 | 11 | 549 |
| Example 9 | 5.2 | 187 |
| Example 10 | 42.6 | 689 |
| Example 11 | 5.3 | 59 |
| Example 12 | 59 | 469 |
| Example 14 | 27 | 767 |
| Example 15 | 125 | 729 |
| Example 16 | 12 | 79 |
| Example 17 | 33 | 599 |
| Example 18 | 205 | 841 |
| Example 19 | 22 | 155 |
| Example 20 | 81 | >1000 |

TABLE 1-continued

| Compound of Example | IC$_{50}$[nM] | |
| --- | --- | --- |
| | ET$_A$ | ET$_B$ |
| Example 21 | 2 | 216 |
| Example 22 | 8.7 | 349 |
| Example 23 | 1.99 | 85 |
| Example 24 | 2.8 | 542 |
| Example 25 | 6.5 | 899 |
| Example 26 | 19 | 881 |
| Example 27 | 2.8 | 153 |
| Example 28 | 2.9 | 595 |
| Example 29 | 8.4 | 402 |
| Example 30 | 2.3 | 111 |
| Example 31 | 1.8 | 180 |
| Example 32 | 11 | >1000 |
| Example 33 | 40 | >1000 |
| Example 34 | 6.5 | 159 |
| Example 35 | 11 | >1000 |
| Example 36 | 1 | 350 |
| Example 37 | 4 | 417 |
| Example 38 | 0.8 | 109 |
| Example 39 | 0.6 | 236 |
| Example 40 | 19 | 636 |
| Example 41 | 28 | 678 |
| Example 42 | 5.7 | 105 |
| Example 43 | 1.6 | 258 |
| Example 44 | 7 | 301 |
| Example 45 | 1 | 69 |
| Example 46 | 1.6 | 185 |
| Example 47 | 2.9 | >1000 |
| Example 48 | 23 | >1000 |
| Example 49 | 2.3 | >1000 |
| Example 50 | 397 | >1000 |
| Example 53 | 1.1 | 824 |
| Example 54 | 18 | >1000 |
| Example 55 | 1.3 | 454 |
| Example 56 | 1.6 | 359 |
| Example 57 | 6.9 | >1000 |
| Example 58 | 0.66 | 838 |
| Example 59 | 6.8 | >1000 |
| Example 60 | 0.8 | 427 |
| Example 61 | 1.1 | 271 |
| Example 62 | 5.5 | >1000 |
| Example 63 | 25 | >1000 |
| Example 64 | 3.5 | >1000 |
| Example 65 | 1.4 | >1000 |
| Example 66 | 1.5 | >1000 |
| Example 67 | 13 | >1000 |
| Example 68 | 1.2 | 563 |
| Example 69 | 1.2 | 314 |
| Example 70 | 0.46 | >1000 |
| Example 71 | 3.6 | >1000 |
| Example 72 | 0.60 | 936 |
| Example 73 | 0.59 | 277 |
| Example 74 | 0.63 | >1000 |
| Example 75 | 3.5 | >1000 |
| Example 76 | 1.1 | >1000 |
| Example 77 | 2.3 | >1000 |
| Example 78 | 10 | >1000 |
| Example 79 | 2.1 | >1000 |
| Example 80 | 1.5 | >1000 |
| Example 81 | 0.54 | >1000 |
| Example 82 | 1.27 | >1000 |
| Example 83 | 0.49 | 640 |
| Example 84 | 0.56 | 118 |

2) Inhibition of Endothelin-Induced Contractions on Isolated Rat Aortic Rings (ET$_A$ Receptors) and Rat Tracheal Rings (ET$_B$ Receptors):

The functional inhibitory potency of the endothelin antagonists was assessed by their inhibition of the contraction induced by endothelin-1 on rat aortic rings (ET$_A$ receptors) and of the contraction induced by sarafotoxin S6c on rat tracheal rings (ET$_B$ receptors). Adult Wistar rats were anesthetized and exsanguinated. The thoracic aorta or trachea were excised, dissected and cut into rings of 3-5 mm length. The endothelium/epithelium was removed by gentle rubbing of the intimal surface. Each ring was suspended in a 10 ml isolated organ bath filled with Krebs-Henseleit solution (in mM; NaCl 115, KCl 4.7, MgSO$_4$ 1.2, KH$_2$PO$_4$ 1.5, NaHCO$_3$ 25, CaCl$_2$ 2.5, glucose 10) kept at 37° C. and gassed with 95% O$_2$ and 5% CO$_2$. The rings were connected to force transducers and isometric tension was recorded (EMKA Technologies SA, Paris, France). The rings were stretched to a resting tension of 3 g (aorta) or 2 g (trachea). Cumulative doses of ET-1 (aorta) or sarafotoxin S6c (trachea) were added after a 10 min incubation with the test compound or its vehicle. The functional inhibitory potency of the test compound was assessed by calculating the concentration ratio, i.e. the shift to the right of the EC$_{50}$ induced by different concentrations of test compound. EC$_{50}$ is the concentration of endothelin needed to get a half-maximal contraction, pA$_2$ is the negative logarithm of the antagonist concentration which induces a two-fold shift in the EC$_{50}$ value.

Because of their ability to inhibit the endothelin binding, the described compounds can be used for treatment of diseases, which are associated with an increase in vasoconstriction, proliferation or inflammation due to endothelin. Examples of such diseases are hypertension, pulmonary hypertension, coronary diseases, cardiac insufficiency, renal and myocardial ischemia, renal failure, cerebral ischemia, dementia, migraine, subarachnoidal hemorrhage, Raynaud's syndrome and portal hypertension. They can also be used in the treatment or prevention of atherosclerosis, restenosis after balloon or stent angioplasty, inflammation, stomach and duodenal ulcer, cancer, prostatic hypertrophy, erectile dysfunction, hearing loss, amaurosis, chronic bronchitis, asthma, gram negative septicemia, shock, sickle cell anemia, glomerulonephritis, renal colic, glaucoma, therapy and prophylaxis of diabetic complications, complications of vascular or cardiac surgery or after organ transplantation, complications of cyclosporin treatment, pain, hyperlipidemia as well as other diseases, presently known to be related to endothelin.

The compounds can be administered orally, rectally, parenterally, e.g. by intravenous, intramuscular, subcutaneous, intrathecal or transdermal administration or sublingually or as ophthalmic preparation or administered as aerosol. Examples of applications are capsules, tablets, orally administered suspensions or solutions, suppositories, injections, eye-drops, ointments or aerosols/nebulizers.

Preferred applications are intravenous, intramuscular, or oral administrations as well as eye drops. The dosage used depends upon the type of the specific active ingredient, the age and the requirements of the patient and the kind of application. Generally, dosages of 0.1-50 mg/kg body weight per day are considered. The preparations with compounds can contain inert or as well pharmacodynamically active excipients. Tablets or granules, for example, could contain a number of binding agents, filling excipients, carrier substances or diluents.

DESCRIPTION OF THE INVENTION

The invention consists of the compounds described in general formula I and their use as endothelin receptor antagonists and especially their use as medicaments for the treatment and prevention of diseases related to the endothelin system:

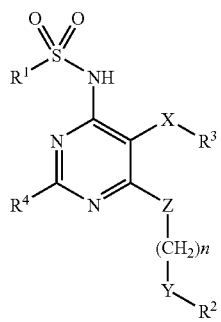

General Formula I wherein
R¹ represents lower alkyl;
R² represents aryl; heteroaryl; lower alkyl;
R³ represents aryl; heteroaryl;
R⁴ represents hydrogen; trifluoromethyl; lower alkyl; lower alkyl-amino; lower alkoxy; lower alkoxy-lower alkoxy; hydroxy-lower alkoxy; lower alkyl-sulfinyl; lower alkylthio; lower alkylthio-lower alkyl; hydroxy-lower alkyl; lower alkoxy-lower alkyl; hydroxy-lower alkoxy-lower alkyl; hydroxy-lower alkyl-amino; lower alkyl-amino-lower alkyl; amino; di-lower alkyl-amino; [N-(hydroxy-lower alkyl)-N-(lower alkyl)]-amino; aryl; aryl-amino; aryl-lower alkyl-amino; aryl-thio; aryl-lower alkyl-thio; aryloxy; aryl-lower alkoxy; aryl-lower alkyl; aryl-sulfinyl; heteroaryl; heteroaryl-oxy; heteroaryl-lower alkyl-oxy; heteroaryl-amino; heteroaryl-lower alkyl-amino; heteroaryl-thio; heteroaryl-lower alkyl-thio; heteroaryl-lower alkyl; heteroaryl-sulfinyl; heterocyclyl; heterocyclyl-lower alkoxy; heterocyclyl-oxy; heterocyclyl-amino; heterocyclyl-lower alkyl-amino; heterocyclyl-thio; heterocyclyl-lower alkyl-thio; heterocyclyl-lower alkyl; heterocyclyl-sulfinyl; cycloalkyl; cycloalkyl-oxy; cycloalkyl-lower alkoxy; cycloalkyl-amino; cycloalkyl-lower alkyl-amino; cycloalkyl-thio; cycloalkyl-lower alkyl-thio; cycloalkyl-lower alkyl; cycloalkyl-sulfinyl;
X represents oxygen; a bond;
Y represents oxygen; —NH—; —NH—SO₂—; —NH—SO₂—NH—; —O—CO—NH—; —NH—CO—O—; —NH—CO—NH—;
Z represents oxygen; sulfur; —NH—;
n represents an integer selected from 2; 3; 4;

and optically pure enantiomers or diastereomers, mixtures of enantiomers or diastereomers, diastereomeric racemates, mixtures of diastereomeric racemates and the meso-forms and pharmaceutically acceptable salts thereof.

In the definitions of the general formula I—if not otherwise stated—the expression lower means straight and branched chain groups with one to seven carbon atoms, preferably 1 to 4 carbon atoms. Examples of lower alkyl and lower alkoxy groups are methyl, ethyl, n-propyl, isopropyl, n-butyl, isobutyl, sec.-butyl, tert.-butyl, pentyl, hexyl, heptyl, methoxy, ethoxy, propoxy, iso-propoxy, butoxy, isobutoxy, sec.-butoxy and tert.-butoxy. Lower alkylendioxy-groups are preferably methylen-dioxy and ethylen-dioxy groups. Examples of lower alkanoyl-groups are acetyl, propanoyl and butanoyl. Lower alkenylen means e.g. vinylen, propenylen and butenylen. Lower alkenyl and lower alkynyl means groups like ethenyl, propenyl, butenyl, 2-methylpropenyl, and ethinyl, propinyl, butinyl, pentinyl, 2-methylpentinyl. Lower alkenyloxy means allyloxy, vinyloxy and propenyloxy. The expression cycloalkyl means a saturated cyclic hydrocarbon ring with 3 to 7 carbon atoms, e.g. cyclopropyl, cyclobutyl, cyclopentyl, cyclohexyl and cycloheptyl, which may be substituted with lower alkyl, hydroxy-lower alkyl, amino-lower alkyl, and lower alkoxy-lower alkyl groups. The expression heterocyclyl means saturated or unsaturated (but not aromatic), four, five-, six- or seven-membered rings containing one or two nitrogen, oxygen or sulfur atoms which may be the same or different and which rings may be adequately substituted with lower alkyl, lower alkoxy, e.g. piperidinyl, morpholinyl, thiomorpholinyl, piperazinyl, tetrahydropyranyl, dihydropyranyl, 1,4-dioxanyl, pyrrolidinyl, tetrahydrofuranyl, dihydropyrrolyl, dihydroimidazolyl, dihydropyrazolyl, pyrazolidinyl and substituted derivatives of such rings with substituents as outlined above. The expression heteroaryl means six-membered aromatic rings containing one to four nitrogen atoms, benzofused six-membered aromatic rings containing one to three nitrogen atoms, five-membered aromatic rings containing one oxygen or one nitrogen or one sulfur atom, benzofused five-membered aromatic rings containing one oxygen or one nitrogen or one sulfur atom, five membered aromatic rings containing an oxygen and nitrogen atom and benzo fused derivatives thereof, five-membered aromatic rings containing a sulfur and a nitrogen atom and benzo fused derivatives thereof, five-membered aromatic rings containing two nitrogen atoms and benzo fused derivatives thereof, five membered aromatic rings containing three nitrogen atoms and benzo fused derivatives thereof or the tetrazolyl ring; e.g. furanyl, thienyl, pyrrolyl, pyridinyl, pyrimidinyl, indolyl, quinolinyl, isoquinolinyl, imidazolyl, triazinyl, thiazinyl, thiazolyl, isothiazolyl, pyridazinyl, oxazolyl, isoxazolyl, 5-oxo-1,2,4-oxadiazolyl, 5-oxo-1,2,4-thiadiazolyl, 5-thioxo-1,2,4-oxadiazolyl, 2-oxo-1,2,3,5-oxathiadiazolyl, whereby such rings may be substituted with lower alkyl, lower alkenyl, amino, amino-lower alkyl, halogen, hydroxy, lower alkoxy, trifluoromethoxy, trifluoromethyl, carboxyl, carboxamidyl, thioamidyl, amidinyl, lower alkoxy-carbonyl, cyano, hydroxy-lower alkyl, lower alkoxy-lower alkyl or another heteroaryl- or heterocyclyl-ring. The expression aryl represents unsubstituted as well as mono-, di- or tri-substituted aromatic rings with 6 to 10 carbon atoms like phenyl or naphthyl rings which may be substituted with aryl, halogen, hydroxy, lower alkyl, lower alkenyl, lower alkynyl, lower alkoxy, lower alkenyloxy, lower alkynyl-lower alkoxy, lower alkenylen, lower alkylenoxy or lower alkylendioxy forming with the phenyl ring a five- or six-membered ring, hydroxy-lower alkyl, hydroxy-lower alkenyl, hydroxy-lower alkyl-lower alkynyl, lower alkoxy-lower alkyl, lower alkoxy-lower alkoxy, trifluoromethyl, trifluoromethoxy, cycloalkyl, hydroxy-cycloalkyl, heterocyclyl, heteroaryl.

The expression pharmaceutically acceptable salts encompasses either salts with inorganic acids or organic acids like hydrohalogenic acids, e.g. hydrochloric or hydrobromic acid; sulfuric acid, phosphoric acid, nitric acid, citric acid, formic acid, acetic acid, maleic acid, tartaric acid, methylsulfonic acid, p-toluolsulfonic acid and the like or in case the compound of formula I is acidic in nature with an inorganic base like an alkali or earth alkali base, e.g. sodium hydroxide, potassium hydroxide, calcium hydroxide and the like.

The compounds of the general formula I might have one or more asymmetric carbon atoms and may be prepared in form of optically pure enantiomers or diastereomers, mixtures of enantiomers or diastereomers, diastereomeric racemates, mixtures of diastereomeric racemates and also in the meso-form. The present invention encompasses all these forms. Mixtures may be separated in a manner known per se, i.e. by column chromatography, thin layer chromatography, HPLC or crystallization.

Because of their ability to inhibit the endothelin binding, the described compounds of the general formula I and their pharmaceutically acceptable salts may be used for treatment of diseases which are associated with an increase in vasoconstriction, proliferation or inflammation due to endothelin. Examples of such diseases are hypertension, coronary diseases, cardiac insufficiency, renal and myocardial ischemia, renal failure, cerebral ischemia, dementia, migraine, subarachnoidal hemorrhage, Raynaud's syndrome, portal hypertension and pulmonary hypertension. They can also be used for the treatment or prevention of atherosclerosis, restenosis after balloon or stent angioplasty, inflammation, stomach and duodenal ulcer, cancer, prostatic hypertrophy, erectile dysfunction, hearing loss, amaurosis, chronic bronchitis, asthma, gram negative septicemia, shock, sickle cell anemia, glomerulonephritis, renal colic, glaucoma, therapy and prophylaxis of diabetic complications, complications of vascular or cardiac surgery or after organ transplantation, complications of cyclosporin treatment, pain, hyperlipidemia as well as other diseases presently known to be related to endothelin.

These compositions may be administered in enteral or oral form e.g. as tablets, dragees, gelatine capsules, emulsions, solutions or suspensions, in nasal form like sprays or rectally in form of suppositories. These compounds may also be administered intramuscularly, parenterally or intravenously, e.g. in form of injectable solutions.

These pharmaceutical compositions may contain the compounds of formula I as well as their pharmaceutically acceptable salts in combination with inorganic and/or organic excipients which are usual in the pharmaceutical industry like lactose, maize or derivatives thereof, talcum, stearinic acid or salts of these materials.

For gelatine capsules vegetable oils, waxes, fats, liquid or half-liquid polyols may be used. For the preparation of solutions and syrups e.g. water, polyols, saccharose, glucose can be used. Injectables can be prepared by using e.g. water, polyols, alcohols, glycerin, vegetable oils, lecithin or liposomes. Suppositories may be prepared by using natural or hydrogenated oils, waxes, fatty acids (fats), liquid or half-liquid polyols.

The compositions may contain in addition preservatives, stability improving substances, viscosity improving or regulating substances, solubility improving substances, sweeteners, dyes, taste improving compounds, salts to change the osmotic pressure, buffer or anti-oxidants.

The compounds of general formula I may also be used in combination with one or more other therapeutically useful substances e.g. α- and β-blockers like phentolamine, phenoxybenzamine, atenolol, propranolol, timolol, metoprolol, carteolol and the like; vasodilators like hydralazine, minoxidil, diazoxide or flosequinan; calcium-antagonists like diltiazem, nicardipine, nimodipine, verapamil or nifedipine; ACE-inhibitors like cilazapril, captopril, enalapril, lisinopril and the like; potassium activators like pinacidil; angiotensin II receptor antagonists like losartan, valsartan, irbesartan and the like; diuretics like hydrochlorothiazide, chlorothiazide, acetolamide, bumetanide, furosemide, metolazone or chlortalidone; sympatholitics like methyldopa, clonidine, guanabenz or reserpine and other therapeutics which serve to treat high blood pressure or any cardiac disorders.

The dosage may vary within wide limits but should be adapted to the specific situation. In general the dosage given daily in oral form should be between about 3 mg and about 3 g, preferably between about 10 mg and about 1 g, especially preferred between 5 mg and 300 mg, per adult with a body weight of about 70 kg. The dosage should be administered preferably in 1 to 3 doses per day which are of equal weight. As usual children should receive lower doses which are adapted to body weight and age.

Preferred compounds are compounds of formula II:

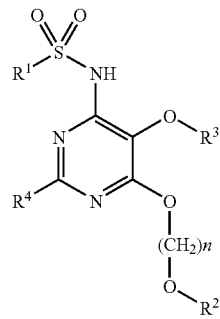

Formula II wherein
$R^1$ represents ethyl; propyl; iso-propyl; butyl;
$R^2$ represents aryl; heteroaryl;
and $R^3$, $R^4$ and n are as defined in general formula I above and optically pure enantiomers or diastereomers, mixtures of enantiomers or diastereomers, diastereomeric racemates, mixtures of diastereomeric racemates and the meso-forms and pharmaceutically acceptable salts thereof.

Also preferred compounds are compounds of formula III:

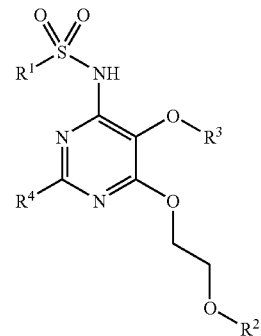

Formula III wherein
$R^1$ represents ethyl; propyl; iso-propyl; butyl;
$R^2$ represents aryl; heteroaryl;
$R^4$ represents hydrogen; heteroaryl;
and $R^3$ is as defined in general formula I above and optically pure enantiomers or diastereomers, mixtures of enantiomers or diastereomers, diastereomeric racemates, mixtures of diastereomeric racemates and the meso-forms and pharmaceutically acceptable salts thereof.

Another group of preferred compounds, are the compounds of formula IV:

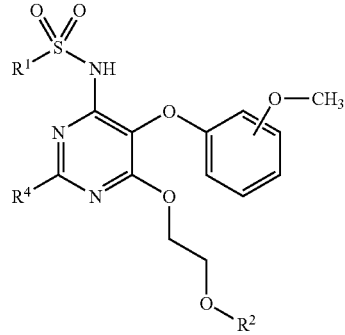

Formula IV wherein
R¹ represents ethyl; propyl; iso-propyl; butyl;
R² represents aryl; heteroaryl;
R⁴ represents hydrogen; heteroaryl;

and optically pure enantiomers or diastereomers, mixtures of enantiomers or diastereomers, diastereomeric racemates, mixtures of diastereomeric racemates and the meso-forms and pharmaceutically acceptable salts thereof.

Another group of preferred compounds, are the compounds of formula V:

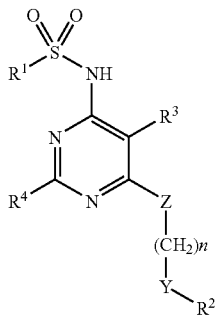

Formula V wherein
R¹, R², R³ and R⁴ as well as Y, Z and n are as defined in general formula I above and optically pure enantiomers or diastereomers, mixtures of enantiomers or diastereomers, diastereomeric racemates, mixtures of diastereomeric racemates and the meso-forms and pharmaceutically acceptable salts thereof.

Also preferred compounds are the compounds of formula VI:

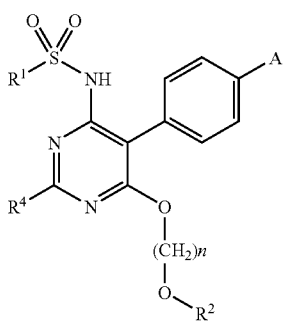

Formula VI wherein
R¹ represents ethyl; propyl; butyl;
R² represents aryl; heteroaryl;
R⁴ represents hydrogen; heteroaryl;
A represents hydrogen; methyl; ethyl; chlorine; bromine;
and n represents the integers 2; 3;

and optically pure enantiomers or diastereomers, mixtures of enantiomers or diastereomers, diastereomeric racemates, mixtures of diastereomeric racemates and the meso-forms and pharmaceutically acceptable salts thereof.

Another group of preferred compounds, are the compounds of formula VI:

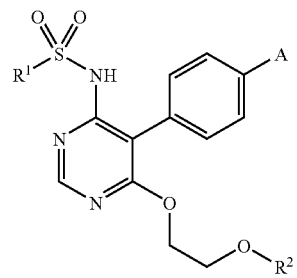

Formula VII wherein
R¹ represents ethyl; propyl; butyl;
R² represents heteroaryl;
A represents methyl; chlorine; bromine;

and optically pure enantiomers or diastereomers, mixtures of enantiomers or diastereomers, diastereomeric racemates, mixtures of diastereomeric racemates and the meso-forms and pharmaceutically acceptable salts thereof.

Preferred compounds are:
Ethanesulfonic acid {6-[2-(5-bromo-pyrimidin-2-yloxy)-ethoxy]-5-p-tolyl-pyrimidin-4-yl}-amide;
n-Propanesulfonic acid {6-[2-(5-bromo-pyrimidin-2-yloxy)-ethoxy]-5-p-tolyl-pyrimidin-4-yl}-amide;
Ethanesulfonic acid [6-[2-(5-bromo-pyrimidin-2-yloxy)ethoxy]-5-(4-chloro-phenyl)-pyrimidin-4-yl]-amide;
n-Propanesulfonic acid [6-[2-(5-bromo-pyrimidin-2-yloxy)-ethoxy]-5-(4-chloro-phenyl)-pyrimidin-4-yl]-amide;
Ethanesulfonic acid {5-(4-bromo-phenyl)-6-[2-(5-bromo-pyrimidin-2-yloxy)-ethoxy]-pyrimidin-4-yl}-amide;
n-Propanesulfonic acid {5-(4-bromo-phenyl)-6-[2-(5-bromo-pyrimidin-2-yloxy)-ethoxy]-pyrimidin-4-yl}-amide;
Ethanesulfonic acid [6-[2-(5-bromo-pyrimidin-2-yloxy)-ethoxy]-5-(2-methoxy-phenoxy)-[2,2']bipyrimidinyl-4-yl]-amide;
n-Propanesulfonic acid [6-[2-(5-bromo-pyrimidin-2-yloxy)-ethoxy]-5-(2-methoxy-phenoxy)-[2,2']bipyrimidinyl-4-yl]-amide;
Ethanesulfonic acid [6-[2-(5-bromo-pyrimidin-2-yloxy)-ethoxy]-5-(2-methoxy-phenoxy)-pyrimidin-4-yl]-amide;
n-Propanesulfonic acid [6-[2-(5-bromo-pyrimidin-2-yloxy)-ethoxy]-5-(2-methoxy-phenoxy)-pyrimidin-4-yl]-amide;
N-[6-[2-(5-Bromo-pyrimidin-2-yloxy)-ethoxy]-5-p-tolyl-pyrimidin-4-yl]-methanesulfonamide;
Ethanesulfonic acid [5-(2-chloro-5-methoxy-phenoxy)-6-[2-(5-methylsulfanyl-pyrimidin-2-yloxy)-ethoxy]-pyrimidin-4-yl]-amide;
Butane-1-sulfonic acid [5-(3-methoxy-phenoxy)-6-[2-(5-methylsulfanyl-pyrimidin-2-yloxy)-ethoxy]-pyrimidin-4-yl]-amide;
Ethanesulfonic acid [5-(4-bromo-phenyl)-6-[2-(5-methylsulfanyl-pyrimidin-2-yloxy)-ethoxy]-pyrimidin-4-yl]-amide;
Propane-1-sulfonic acid [5-(2-chloro-5-methoxy-phenoxy)-6-[2-(5-methylsulfanyl-pyrimidin-2-yloxy) ethoxy]-pyrimidin-4-yl]-amide;

Especially preferred compounds are:
N-[5-(4-Bromo-phenyl)-6-[2-(5-bromo-pyrimidin-2-yloxy)ethoxy]-pyrimidin-4-yl]-methanesulfonamide;

Ethanesulfonic acid [5-(4-bromo-phenyl)-6-[2-(5-bromo-pyrimidin-2-yloxy)-ethoxy]-pyrimidin-4-yl]-amide;
Propane-1-sulfonic acid [5-(4-bromo-phenyl)6-[2-(5-bromo-pyrimidin-2-yloxy)-ethoxy]-pyrimidin-4-yl]-amide;
Propane-1-sulfonic acid [6-[2-(5-bromo-pyrimidin-2-yloxy)-ethoxy]-5-(2-methoxy-phenoxy)-pyrimidin-4-yl]-amide;
Ethanesulfonic acid [6-[2-(5-methylsulfanyl-pyrimidin-2-yloxy)-ethoxy]-5-p-tolyl-pyrimidin-4-yl]-amide;
Propane-1-sulfonic acid [5-(4-bromo-phenyl)-6-[2-(5-methylsulfanyl-pyrimidin-2-yloxy)-ethoxy]-pyrimidin-4-yl]-amide;
Ethanesulfonic acid [6-[2-(5-bromo-pyrimidin-2-yloxy)-ethoxy]-5-(2-chloro-5-methoxy-phenoxy)-pyrimidin-4-yl]-amide;
Propane-1-sulfonic acid [6-[2-(5-bromo-pyrimidin-2-yloxy)-ethoxy]-5-(2-chloro-5-methoxy-phenoxy)-pyrimidin-4-yl]-amide;

Compounds of the general formula I of the present invention can be prepared according to the general sequence of reactions retro-synthetically outlined below. For simplicity and clarity reasons sometimes only parts of the synthetic possibilities which lead to compounds of general formula I are described. The literature references given in brackets [ ] are set forth at the end of this paragraph.

Retro-synthetic scheme:

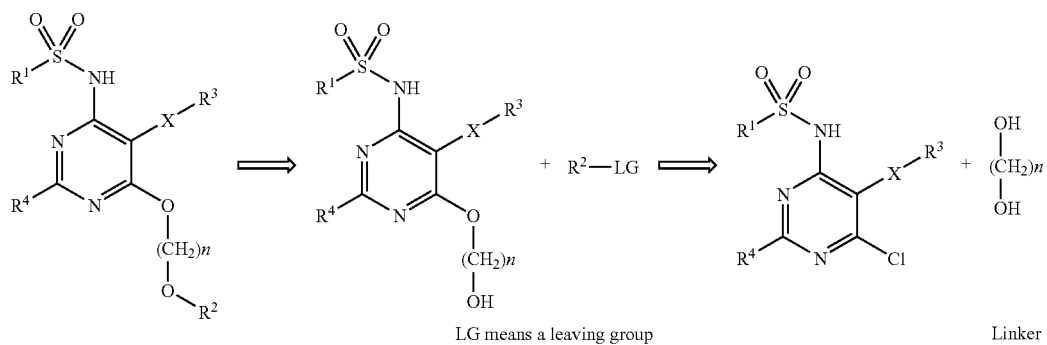

LG means a leaving group

Linker

The sulfonamides and the dichloropyrimidines were prepared according to procedures described in the literature [3], [5], [6], [10].

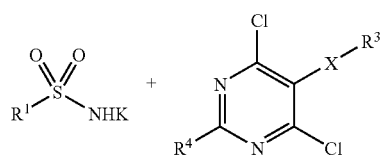

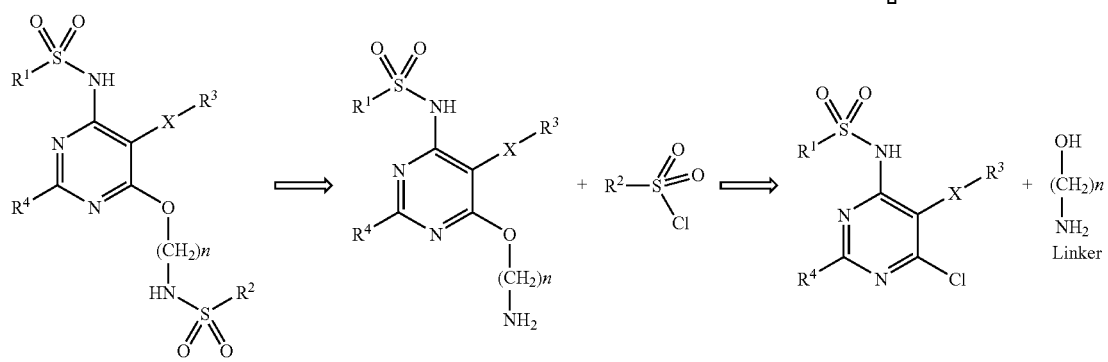

Linker

As a general different synthetic possibility, in certain cases the side-chain should first be prepared (especially when $R_2$ represents aryl) and only then the whole side chain should be attached to the pyrimidine core.

-continued
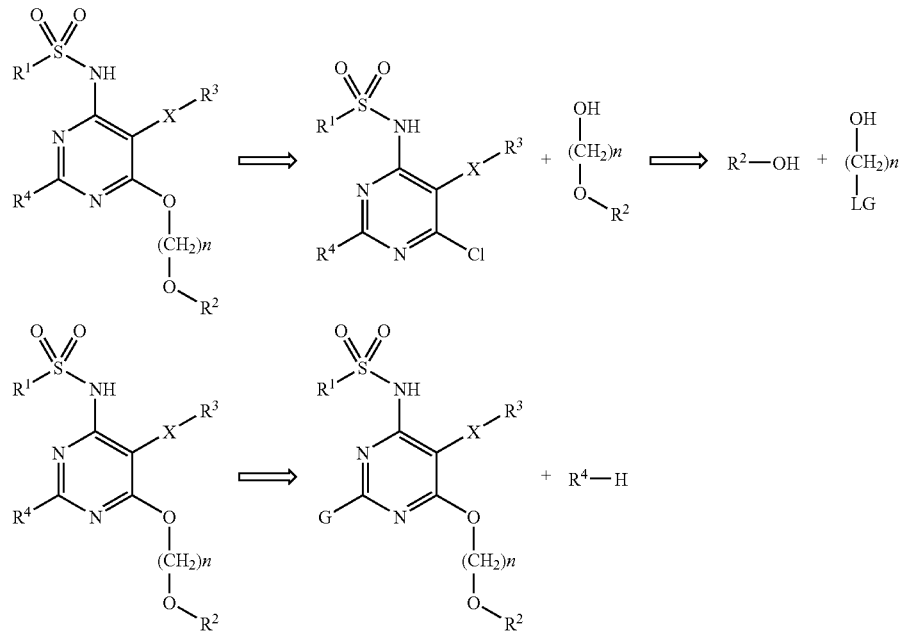
G represents a leaving group like alkylsulfonyl, phenylsulfonyl or halogen.
R⁴ represents:
Scheme 1: Schematically exemplified synthesis of Examples 1, 2 and 3:
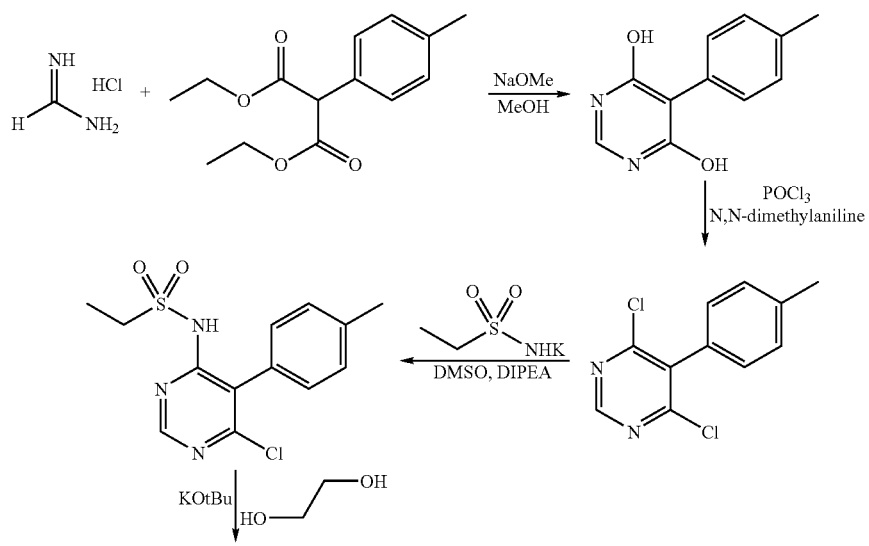

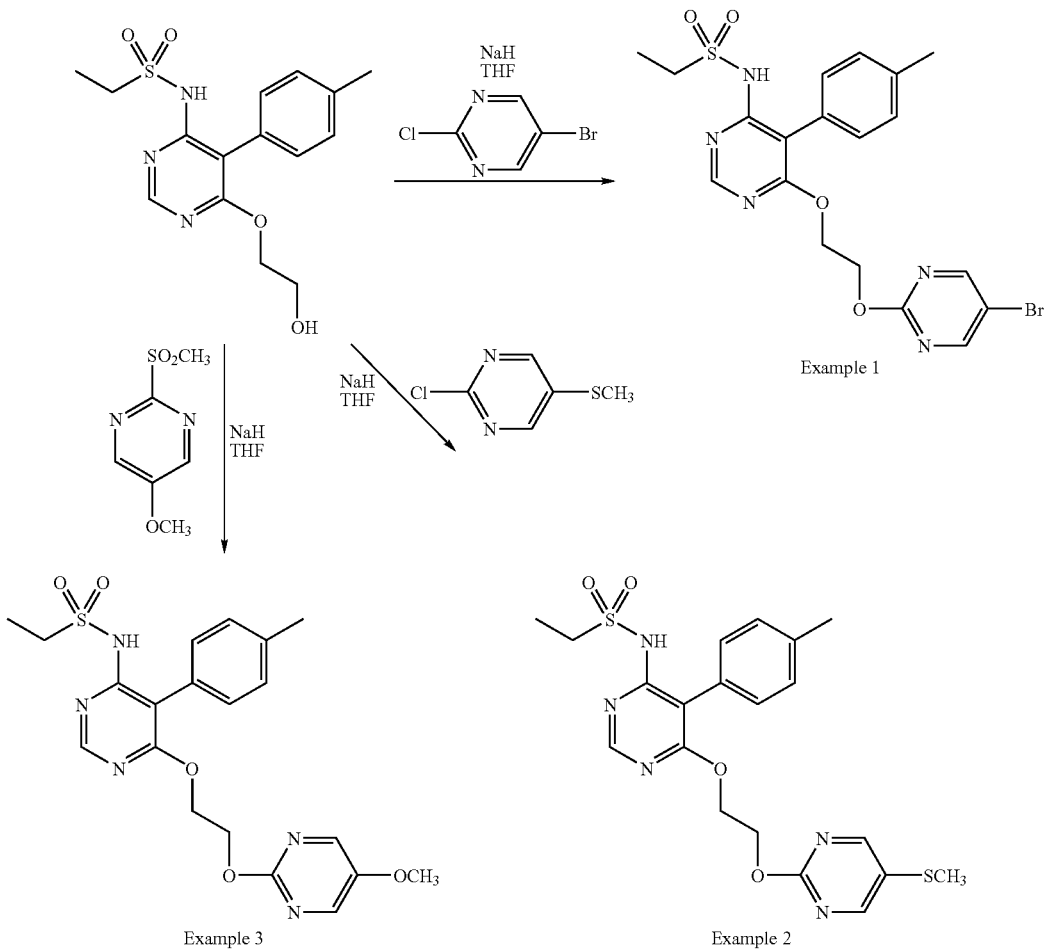
Example 1
Example 3
Example 2
Scheme 2: Schematically exemplified synthesis of Examples 4, 5 and 6:
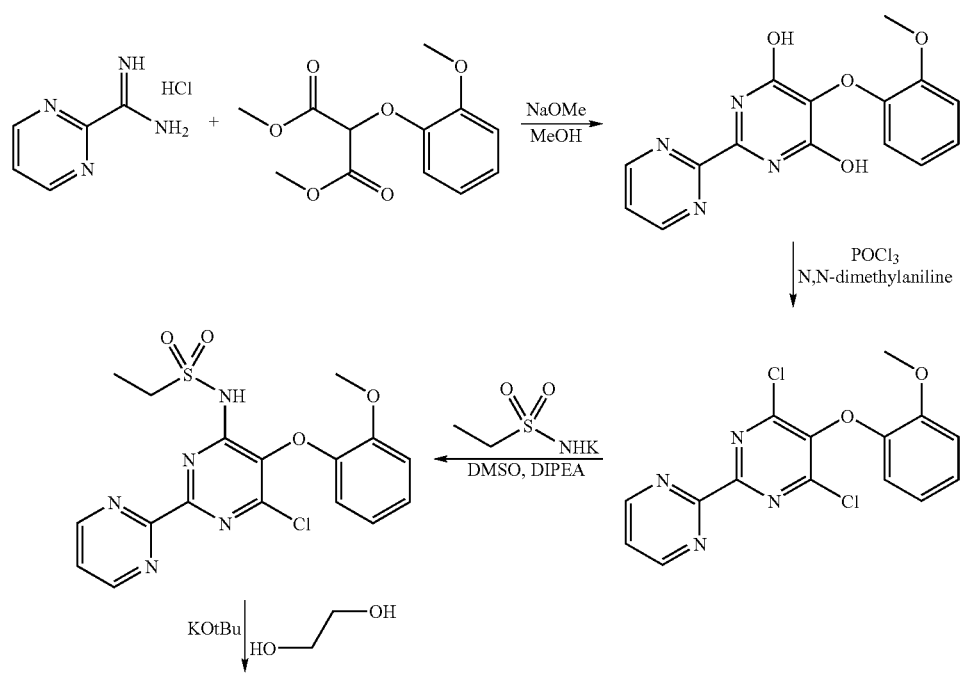

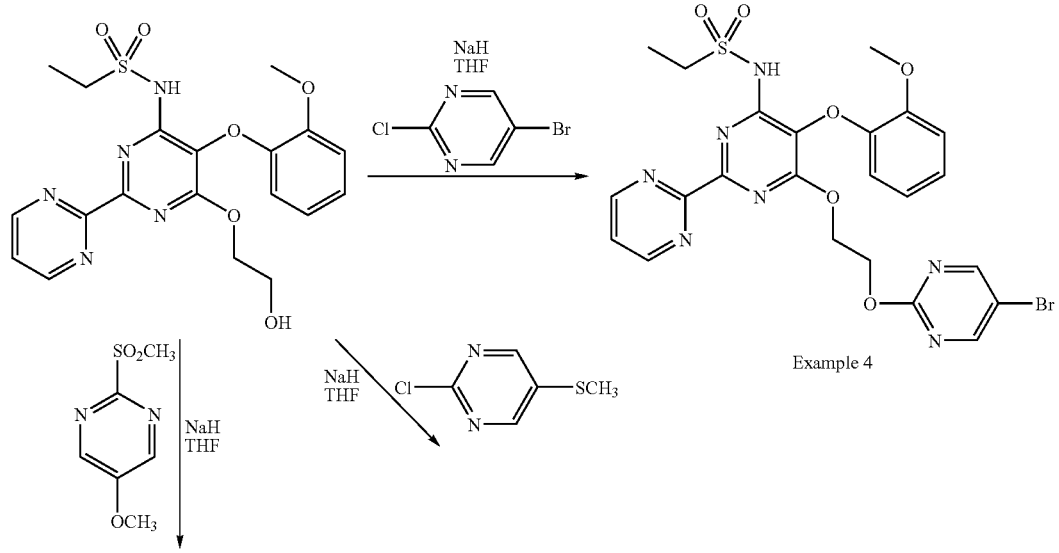
Example 4
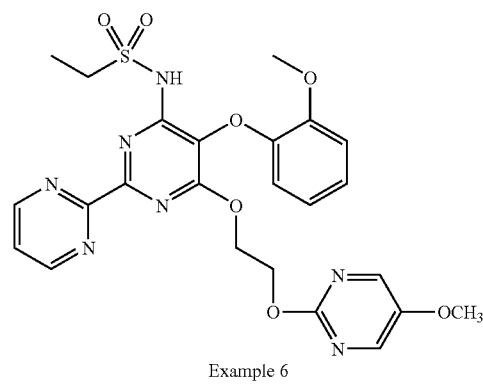
Example 6
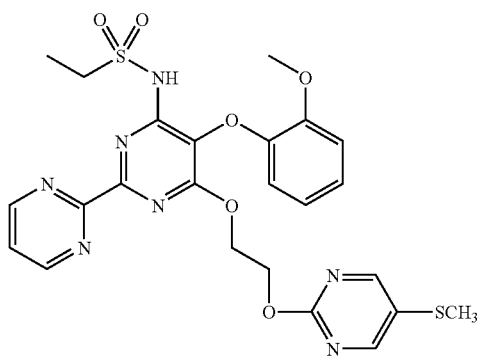
Example 5
Scheme 3: Preparation of Substituted pyrimidines [9], [10]:
a)
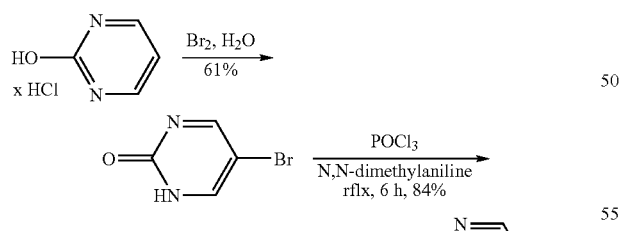
b)
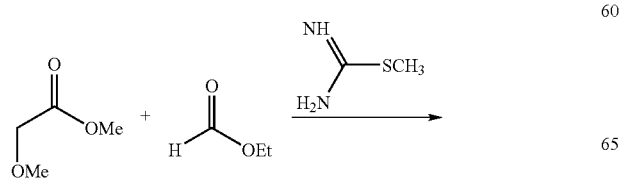
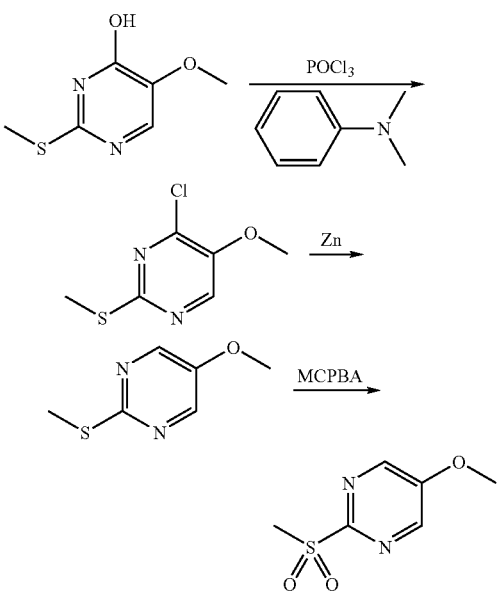

-continued c)

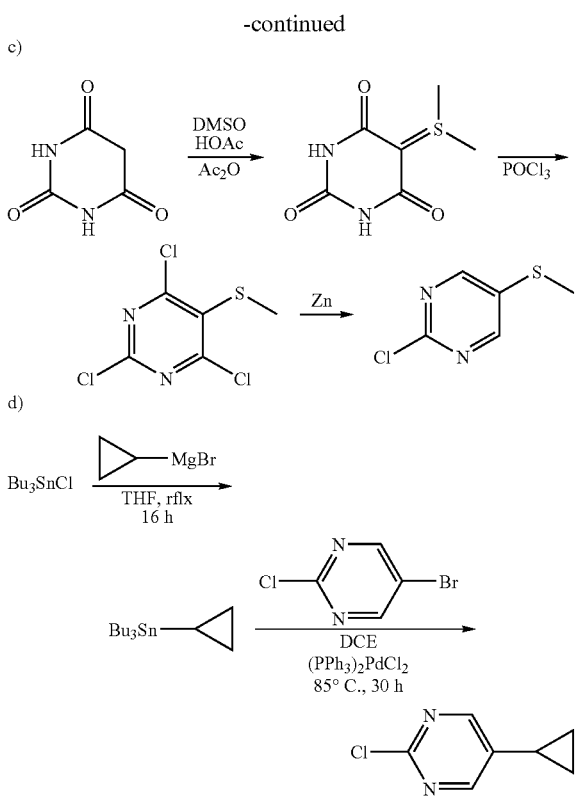

d)

Scheme 4: Preparation of the precursors for the synthesis of compounds of general formula I wherein X represents a bond [5]:

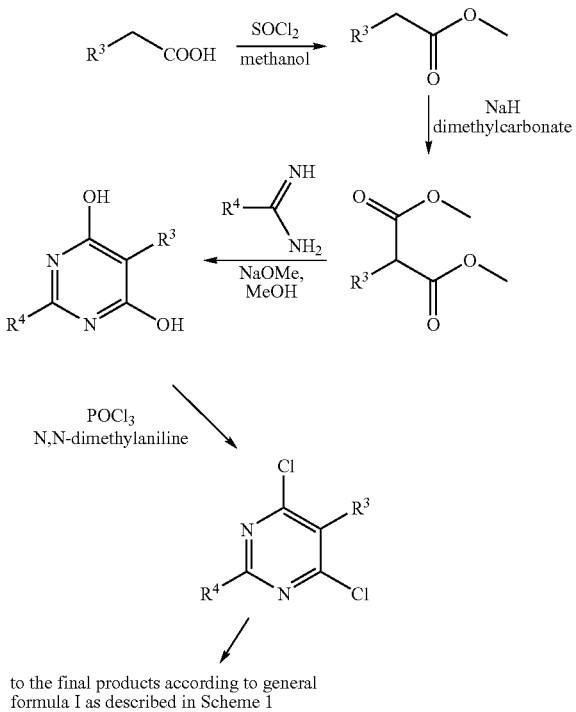

to the final products according to general formula I as described in Scheme 1

In Scheme 4 the symbols $R^3$ and $R^4$ represent the same as defined in general formula I above.

REFERENCES

[1] W. Göhring, J. Schildknecht, M. Federspiel; *Chimia*, 1996, 50, 538-543.
[2] W. Neidhart, V. Breu, D. Bur, K. Burri, M. Clozel, G. Hirth, M. Müller, H. P. Wessel, H. Ramuz; *Chimia*, 1996, 50, 519-524 and references cited there.
[3] W. Neidhart, V. Breu, K. Burri, M. Clozel, G. Hirth, U. Klinkhammer, T. Giller, H. Ramuz; *Bioorg. Med. Chem. Lett.*, 1997, 7, 2223-2228. R. A. Nugent, S. T. Schlachter, M. J. Murphy, G. J. Cleek, T. J. Poel, D. G. Whishka, D. R. Graber, Y. Yagi, B. J. Keiser, R. A. Olmsted, L. A. Kopta, S. M. Swaney, S. M. Poppe, J. Morris, W. G. Tarpley, R. C. Thomas; *J. Med. Chem.*, 1998, 41, 3793-3803.
[4] J. March; *Advanced Organic Chemistry*, 4$^{th}$ Ed., 1994, p. 499 and references cited there.
[5] EP 0 743 307 A1; EP 0 658 548 B1; EP 0 959 072 A1 (Tanabe Seiyaku)
[6] EP 0 633 259 B1; EP 0 526 708 A1; WO 96/19459 (F. Hoffmann-LaRoche)
[7] for the Synthesis of 5-membered heterocycles see: Y. Kohara et al; *J. Med. Chem.*, 1996, 39, 5228-5235 and references cited there.
[8] EP 0 882 719 A1 (Yamanouchi Pharmaceutical Co., Ltd)
[9] D. G. Crosby, R. V. Berthold; *J. Org. Chem.*, 1960; 25; 1916.
[10] U.S. Pat. No. 4,233,294, 1980, (Bayer AG);
[11] WO 01/17976; WO 01/46156; WO 01/81335; WO 01/81338; WO 02/24665; WO 02/208200 (Actelion Pharmaceuticals Ltd).

EXAMPLES

The following examples illustrate the invention. All temperatures are stated in ° C.

List of Abbreviations:
CyHex cyclohexane
DBU 1,8-diazabicyclo[5.4.0]undec-7-en(1,5-5)
DCM dichloromethane
DIPEA diisopropylethylamine
DMAP 4-dimethylaminopyridine
DMF dimethylformamide
DMSO dimethylsulfoxide
EtOAc ethyl acetate
Hex hexane
HV high vacuum conditions
MCPBA m-chloroperbenzoic acid
min minutes
rflx reflux
rt room temperature
THF tetrahydrofuran
$t_R$ retention time.

The following compounds were prepared according to the procedure described above and shown in Schemes 1 to 4. All compounds were characterized by 1H-NMR (300 MHz) and occasionally by 13C-NMR (75 MHz) (Varian Oxford, 300 MHz; chemical shifts are given in ppm relative to the solvent used; multiplicities: s=singlet, d=doublet, t=triplet; m=multiplet), by LC-MS (Waters Micromass; ZMD-platform with ESI-probe with Alliance 2790 HT; Column: 2×30 mm, Gromsil ODS4, 3 µm, 120 A; Gradient: 0-100% acetonitril in water, 6 min, with 0.05% formic acid, flow: 0.45 ml/min; $t_R$ is given in min.) or by Finnigan Navigator (LC-MS$^1$) with HP 1100 Binary Pump and DAD, column: 4.6×50 mm, Develosil RP Aqueous, 5 µm, 120 A, gradient:

Example 1

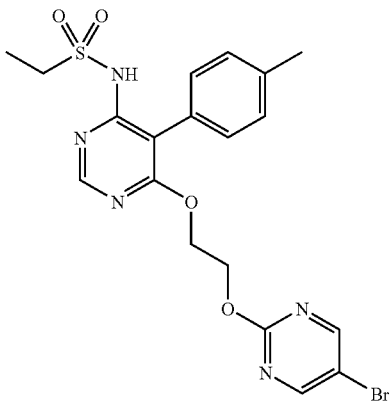

a) At 0° C. a solution of diethyl 2-(p-tolyl)-malonate (14.2 g) in methanol (50 ml) was slowly added to a solution of sodium methylate (9.4 g) in methanol (300 ml). Upon completion of the addition the reaction mixture was allowed to warm up and formamidine hydrochloride (5.4 g) was added. The mixture was stirred at rt for 16 h. The solvent was removed under reduced pressure and the remaining residue was treated with 2 N hydrochloric acid (150 ml). The suspension was stirred for 0.5 h. At 0-5° C., the pH was carefully adjusted to 4 using 10 N sodium hydroxide solution. The precipitate was collected, washed with cold water, isopropanol, and diethyl ether and dried under high vacuum at 65° C. to give 4,6-dihydroxy-5-(p-tolyl)-pyrimidine (11.2 g) (or a tautomer) as a white powder.

b) At rt N,N-dimethylaniline (10 ml) was added to a mixture of 4,6-dihydroxy-5-(p-tolyl)-pyrimidine (5.1 g) and $POCl_3$ (75 ml). The reaction mixture was stirred at 70° C. for 16 h. The excess of $POCl_3$ was distilled off and the remaining oil was treated with an ice:water mixture and extracted three times with diethyl ether. The combined organic extracts were washed with 1N aqueous hydrochloric acid followed by brine, dried over $MgSO_4$ and evaporated. The remaining brown oil was crystallised from isopropanol. The pale yellow crystals were collected, washed with cold isopropanol and dried under high vacuum to furnish 4,6-dichloro-5-(p-tolyl)-pyrimidine (4.1 g).

c) Ethanesulfonyl chloride (24 g) was dissolved in THF (30 ml) and cooled to 0° C. Then ammonium hydroxide solution (25%, 40 ml) was added via addition funnel followed by stirring at rt for 1 h. The THF was removed under reduced pressure and the remaining solution was extracted with ethyl acetate. The combined organic layers were dried over magnesium sulfate and concentrated in vacuo to give ethanesulfonamide (7.2 g) as an oil which was dissolved in MeOH (100 ml) followed by the addition of potassium tert.-butoxide (7.4 g) and stirring for 30 min. The solvent was evaporated and the residue was washed with diethyl ether and dried at HV to give ethanesulfonamide potassium salt (9.7 g) as a white, hygroscopic powder.

d) 4,6-dichloro-5-(p-tolyl)-pyrimidine (717 mg) was dissolved in DMSO (5 ml) and ethanesulfonamide potassium salt (927 mg) was added and stirring continued for 14 h at rt. The solution was poured onto ice/water and acidified by 2 N HCl to pH 3-4. The precipitate was filtered off and washed with water and diethylether to give ethanesulfonic acid (6-chloro-5-p-tolyl-pyrimidin-4-yl)-amide (370 mg) as a white powder. LC-MS: $t_R$: 4.09, $[M+H]^+$: 312.10.

e) Ethanesulfonic acid (6-chloro-5-p-tolyl-pyrimidin-4-yl)-amide (363 mg) was added to a solution of potassium tert.-butoxide (427 mg) in ethylene glycol (7 ml) and stirred at 100° C. for 7 days. The reaction mixture was then poured onto ice/water and extracted with ethyl acetate. The crude product was purified by chromatography over silicagel with DCM/MeOH=9/1 to give ethanesulfonic acid [6-(2-hydroxy-ethoxy)-5-p-tolyl-pyrimidin-4-yl]-amide (310 mg) as a white powder. LC-MS: $t_R$: 3.47, $[M+H]^+$: 338.13.

f) Ethanesulfonic acid [6-(2-hydroxy-ethoxy)-5-p-tolyl-pyrimidin-4-yl]-amide (135 mg) was dissolved in THF (15 ml) and sodium hydride (80 mg) was added followed by stirring for 15 min at 50° C. Then 2-chloro-5-bromo-pyrimidine (162 mg) was added and stirring was continued for 8 h at 70 C. The reaction mixture was poured onto ice water, acidified with solid citric acid and extracted with ethylacetate. The combined organic extracts were dried over magnesium sulfate and the solvent was evaporated. The crude material was purified by plate chromatography with ethyl acetate/hexane=½ to give ethanesulfonic acid {6-[2-(5-bromo-pyrimidin-2-yloxy)-ethoxy]-5-p-tolyl-pyrimidin-4-yl}-amide (68 mg) as a white powder. LC-MS: $t_R$: 4.64, $[M+H]^+$: 496.19.

Example 2

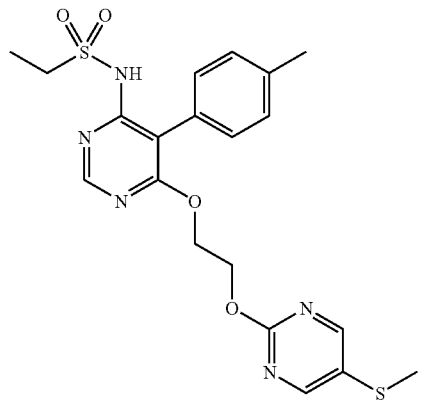

According to the procedure described in Example 1f) ethanesulfonic acid {6-[2-(5-methylsulfanyl-pyrimidin-2-yloxy)-ethoxy]-5-p-tolyl-pyrimidin-4-yl}-amide (73 mg) was prepared by reaction of ethanesulfonic acid [6-(2-hydroxy-ethoxy)-5-p-tolyl-pyrimidin-4-yl]-amide (84 mg) with 2-chloro-5-sulfanyl-pyrimidine (130 mg). LC-MS: $t_R$: 4.55, $[M+H]^+$: 462.24.

Example 3

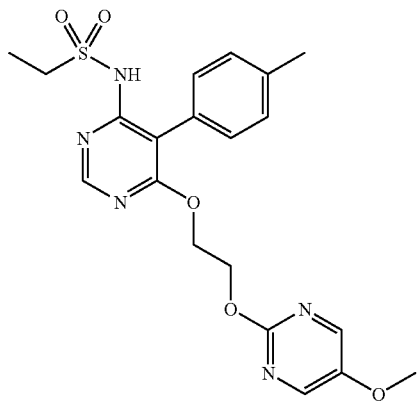

According to the procedure described in Example 1f) ethanesulfonic acid {6-[2-(5-methoxy-pyrimidin-2-yloxy)-ethoxy]-5-p-tolyl-pyrimidin-4-yl}-amide (65 mg) was prepared by reaction of ethanesulfonic acid [6-(2-hydroxy-ethoxy)-5-p-tolyl-pyrimidin-4-yl]-amide (84 mg) with 2-sulfono-5-methoxy-pyrimidine (103 mg). LC-MS: $t_R$: 4.25, [M+H]$^+$: 446.35.

Example 4

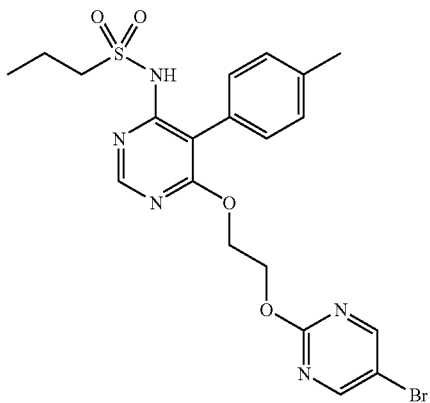

a) n-Propane sulfonyl chloride (20.7 g) was dissolved in THF (40 ml) and cooled to 0° C. Then ammonium hydroxide solution (25%, 40 ml) was added via addition funnel followed by stirring at rt for 1 h. The THF was removed under reduced pressure and the remaining solution was extracted with ethyl acetate. The combined organic extracts were dried over magnesium sulfate and concentrated in vacuo to give n-propane sulfonamide (10.99 g) as an oil which was dissolved in MeOH (100 ml) followed by the addition of potassium tert.-butoxide (10.6 g) and stirring for 30 min. The solvent was evaporated and the residue was triturated with diethyl ether. The white solid was isolated by filtration and dried at HV to give n-propanesulfonamide potassium salt (13.4 g) as a white, hygroscopic powder.

b) To a solution of 4,6-dichloro-5-(p-tolyl)pyrimidine (Example 1b; 717 mg) in DMSO (5 ml) and n-propane-sulfonamide potassium salt (1016 mg) was added. Stirring was continued for 14 h at rt. The solution was poured onto ice/water and acidified by 2 N HCl to pH 3-4. The precipitate was filtered off and washed with water and diethylether to give n-propanesulfonic acid (6-chloro-5-p-tolyl-pyrimidin-4-yl)-amide (765 mg) as a white powder. LC-MS: $t_R$: 4.44, [M+H]$^+$: 326.13.

c) n-Propanesulfonic acid (6-chloro-5-p-tolyl-pyrimidin-4-yl)-amide (489 mg) was added to a solution of potassium tert.-butoxide (900 mg) in ethylene glycol (10 ml). The solution was stirred at 100° C. for 7 days. The reaction mixture was then poured onto ice/water and extracted with ethyl acetate. The crude product was purified by chromatography over silicagel with DCM/MeOH=9/1 to give n-propanesulfonic acid [6-(2-hydroxy-ethoxy)-5-p-tolyl-pyrimidin-4-yl]-amide (390 mg) as a white powder. LC-MS: $t_R$: 3.76, [M+H]$^+$: 352.13.

d) n-Propanesulfonic acid [6-(2-hydroxy-ethoxy)-5-p-tolyl-pyrimidin-4-yl]-amide (115 mg) was dissolved in THF (15 ml). Sodium hydride (60 mg) was added followed by stirring for 15 min at 50° C. Then 2-chloro-5-bromo-pyrimidine (135 mg) was added and stirring was continued for 8 h at 75° C. The reaction mixture was poured onto ice water, acidified with solid citric acid and extracted with ethyl acetate. The combined organic extracts were dried over magnesium sulfate, filtered and the solvent was evaporated. The crude material was purified by plate chromatography with diethyl ether to give n-propanesulfonic acid {6-[2-(5-bromo-pyrimidin-2-yloxy)-ethoxy]-5-p-tolyl-pyrimidin-4-yl}-amide (65 mg) as a white powder. LC-MS: $t_R$: 4.91, [M+H]$^+$: 510.13.

Example 5

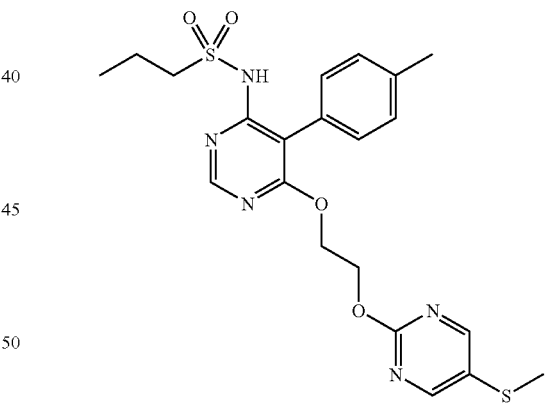

n-Propanesulfonic acid [6-(2-hyroxy-ethoxy)-5-p-tolyl-pyrimidin-4-yl]-amide (88 mg) was dissolved in THF (10 ml) and sodium hydride (46 mg) was added followed by stirring for 15 min at 50° C. Then 2-chloro-5-methylsulfanyl-pyrimidine (88 mg) was added and stirring was continued for 8 h at 75° C. The reaction mixture was poured onto ice water, acidified with solid citric acid and extracted with ethylacetate. The combined organic extracts were dried over magnesium sulfate and the solvent was evaporated. The crude material was recrystallized from methanol to give propane-1-sulfonic acid {6-[2-(5-methylsulfanyl-pyrimidin-2-yloxy)-ethoxy]-5-p-tolyo-pyrimidin-4-yl}-amide (64 mg) as a white powder. LC-MS: $t_R$: 4.82, [M+H]$^+$: 476.29.

Example 6

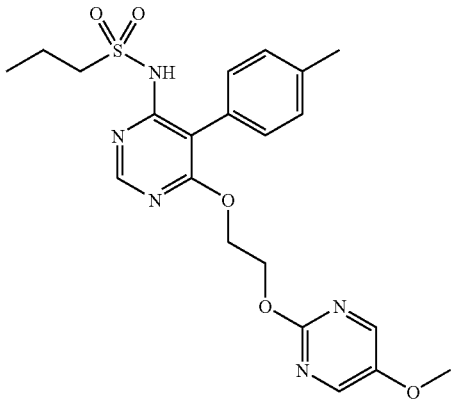

n-Propanesulfonic acid [6-(2-hydroxy-ethoxy)-5-p-tolyl-pyrimidin-4-yl]-amide (115.5 mg) was dissolved in THF (10 ml) and sodium hydride (60 mg) was added followed by stirring for 15 min at 50° C. Then 2-methanesulfonyl-5-methoxy-pyrimidine (138 mg) was added and stirring was continued for 8 h at 75° C. The reaction mixture was poured onto ice water, acidified with solid citric acid and extracted with ethyl acetate. The combined organic layers were dried over magnesium sulfate and the solvent was evaporated. The crude material was purified by plate chromatography with diethyl ether to give propane-1-sulfonic acid {6-[2-(5-methoxy-pyrimidin-2-yloxy)-ethoxy]-5-p-tolyl-pyrimidin-4-yl}-amide (61 mg) as a white powder. LC-MS: $t_R$: 4.51, [M+H]$^+$: 460.27.

Example 7

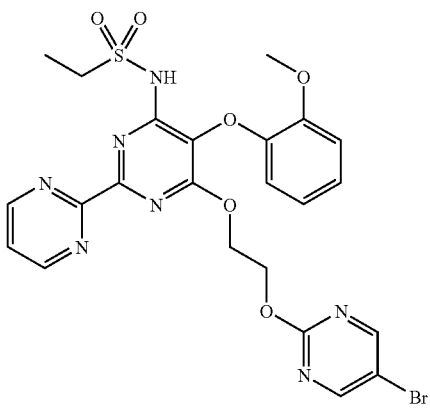

a) To a solution of 4,6-dichloro-5-(2-methoxy-phenoxy)-[2,2']bipyrimidinyl (prepared as described in [6] and [11]) (1.74 g) in DMSO (5 ml) was added ethanesulfonamide potassium salt (1.62 g). Stirring was continued for 10 days at rt. The reaction mixture was poured onto ice/water and acidified by 2N HCl. The precipitate was filtered off, washed with water and dried at HV to give ethanesulfonic acid [6-chloro-5-(2-methoxy-phenoxy)-[2,2']bipyrimidinyl-4-yl]-amide (1.75 g) as a white powder. LC-MS: $t_R$: 3.77, [M+H]$^+$: 422.15.

b) To a solution of potassium tert.-butoxide (366.5 mg) in ethylene glycol (5 ml) was added 1,2-dimethoxy ethane (5 ml) and ethanesulfonic acid [6-chloro-5-(2-methoxy-phenoxy)-[2,2']bipyrimidinyl-4-yl]-amide (420 mg). The reaction mixture was heated to 85° C. for 7 days, concentrated in vacuo, poured onto water, acidified by 2N HCl, and extracted with ethyl acetate. The combined organic extracts were dried over magnesium sulfate and concentrated in vacuo. The precipitated product was washed with diethyl ether, filtered and dried at HV to give ethanesulfonic acid [6-(2-hydroxy-ethoxy)-5-(2-methoxy-phenoxy)-[2,2']bipyrimidinyl-4-yl]-amide (400 mg). LC-MS: $t_R$: 3.45, [M+H]$^+$: 448.24.

c) Ethanesulfonic acid [6-(2-hydroxy-ethoxy)-5-(2-methoxy-phenoxy)-[2,2]bipyrimidinyl-4-yl]-amide (89 mg) was dissolved in THF (10 ml). Sodium hydride (60 mg) and 2-chloro-5-bromo-pyrimidine (100 mg) were added and the mixture was heated to 75° C. for 48 h, then poured onto water, acidified with solid citric acid and the precipitate was filtered off. The crude material was purified by crystallization from methanol to give ethanesulfonic acid [6-[2-(5-bromo-pyrimidin-2-yloxy)-ethoxy]-5-(2-methoxy-phenoxy)-[2,2']bipyrimidinyl-4-yl]-amide (54 mg) as a white powder. LC-MS: $t_R$: 4.23, [M+H]$^+$: 605.90.

Example 8

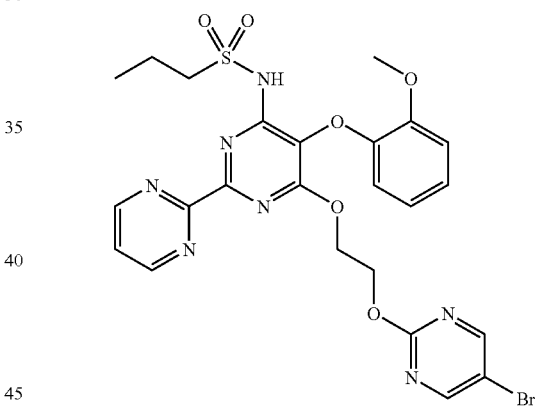

a) To a solution of 4,6-dichloro-5-(2-methoxy-phenoxy)-[2,2']bipyrimidinyl (prepared as described in [6] and [11]) (1.74 g) in DMSO (5 ml) was added n-propanesulfonamide potassium salt (1.77 g). Stirring was continued for 10 days at rt. The reaction mixture was poured onto ice/water and acidified by 2N HCl. The precipitate was filtered off, washed with water and dried at HV to give n-propanesulfonic acid [6-chloro-5-(2-methoxy-phenoxy)-[2,2']bipyrimidinyl-4-yl]-amide (2.17 g) as a white powder. LC-MS: $t_R$: 4.14, [M+H]$^+$: 434.13.

b) To a solution of potassium tert.-butoxide (366.5 mg) in ethylene glycol (5 ml) was added 1,2-dimethoxy ethane (5 ml) and n-propanesulfonic acid [6-chloro-5-(2-ethoxy-phenoxy)-[2,2']bipyrimidinyl-4-yl]amide (420 mg). The reaction mixture was heated to 85° C. for 7 days, concentrated in vacuo, poured onto water, acidified by 2N HCl and extracted with ethyl acetate. The combined organic extracts were dried over magnesium sulfate and concentrated in vacuo. The precipitated product was washed with diethyl-ether, filtered and dried at HV to give n-propanesulfonic acid

[6-(2-hydroxy-ethoxy)-5-(2-methoxy-phenoxy)-[2,2']bipyrimidinyl-4-yl]-amide (401 mg). LC-MS: $t_R$: 3.67, [M+H]$^+$: 462.26.

c) n-Propanesulfonic acid [6-(2-hydroxy-ethoxy)-5-(2-methoxy-phenoxy)-[2,2']bipyrimidinyl-4-yl]-amide (92 mg) was dissolved in THF (10 ml). Sodium hydride (60 mg) and 2-chloro-5-bromo-pyrimidine (85 mg) were added and the mixture was heated to 75 C for 16 h, then poured onto water, acidified with solid citric acid and the precipitate was filtered off. The crude material was purified by crystallization from methanol to give n-propanesulfonic acid [6-[2-(5-bromo-pyrimidin-2-yloxy)-ethoxy]-5-(2-methoxy-phenoxy)-[2,2']bipyridinyl-4-yl]-amide (54 mg) as a white powder. LC-MS: $t_R$: 4.44, [M+H]$^+$: 619.77.

Example 9

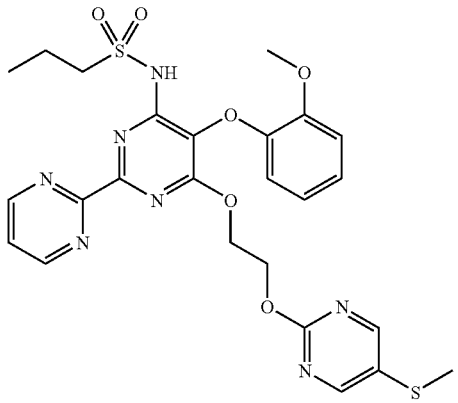

n-Propanesulfonic acid [6-(2-hydroxy-ethoxy)-5-(2-methoxy-phenoxy)-[2,2']bipyrimidinyl-4-yl]-amide (92 mg) was dissolved in THF (6 ml). Sodium hydride (40 mg) and 2-chloro-5-methylsulfanyl-pyrimidine (71 mg) were added and the mixture was heated to 75° C. for 6 h, then poured onto water, acidified with solid citric acid and the precipitate was filtered off. The crude material was purified by crystallization from methanol to give n-propanesulfonic acid [6-[2-(5-methylsulfanyl-pyrimidin-2-yloxy)-ethoxy]-5-(2-methoxy-phenoxy)-[2,2']bipyrimidinyl-4-yl]-amide (61 mg) as a white powder. LC-MS: $t_R$: 4.37, [M+H]$^+$: 586.19.

Example 10

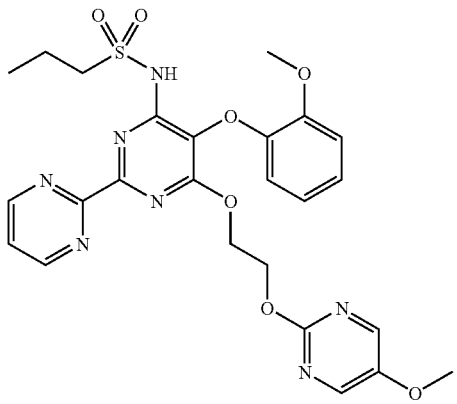

n-Propanesulfonic acid [6-(2-hydroxy-ethoxy)-5-(2-methoxy-phenoxy)-[2,2']bipyrimidinyl-4-yl]-amide (92 mg) was dissolved in THF (6 ml). Sodium hydride (40 mg) and 2-chloro-5-methoxy-pyrimidine (92 mg) were added and the mixture was heated to 75° C. for 6 h, then poured onto water, acidified with solid citric acid and the precipitate was filtered off. The crude material was purified by crystallization from methanol to give n-propanesulfonic acid [6-[2-(5-methoxy-pyrimidin-2-yloxy)-ethoxy]-5-(2-methoxy-phenoxy)-[2,2']bipyrimidinyl-4-yl]-amide (61 mg) as a white powder. LC-MS: $t_R$: 4.10, [M+H]$^+$: 570.22.

Example 11

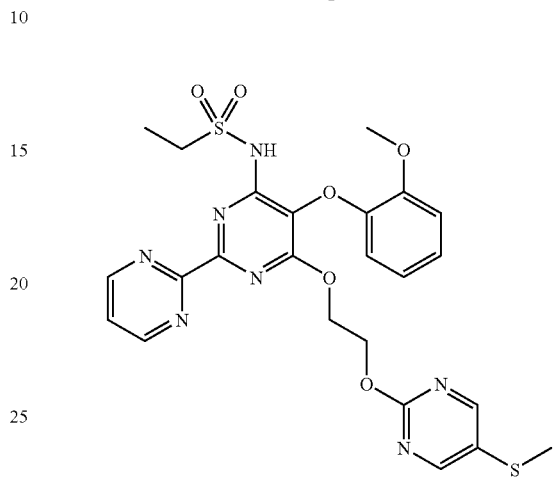

Ethanesulfonic acid [6-(2-hydroxy-ethoxy)-5-(2-methoxy-phenoxy)-[2,2']bipyrimidinyl-4-yl]-amide (89 mg) was dissolved in THF (6 ml). Sodium hydride (40 mg) and 2-chloro-5-methylsulfanyl-pyrimidine (71 mg) were added and the mixture was heated to 75° C. for 48 h, then poured onto water, acidified with solid citric acid and the precipitate was filtered off. The crude material was purified by crystallization from methanol to give ethanesulfonic acid [6-[2-(5-methylsulfanyl-pyrimidin-2-yloxy)-ethoxy]-5-(2-methoxy-phenoxy)-[2,2']bipyrimidinyl-4-yl]-amide (58 mg) as a white powder. LC-MS: $t_R$: 4.15, [M+H]$^+$: 572.19.

Example 12

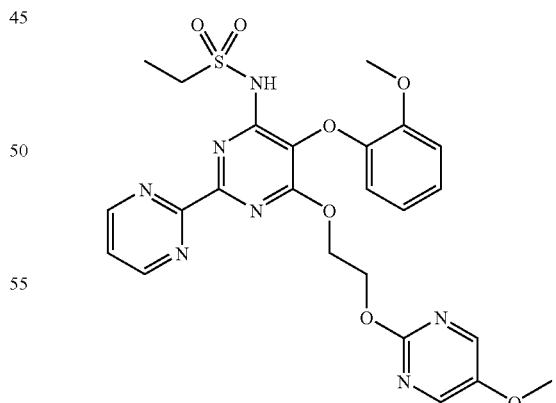

Ethanesulfonic acid [6-(2-hydroxy-ethoxy)-5-(2-methoxy-phenoxy)-[2,2']bipyrimidinyl-4-yl]-amide (89 mg) was dissolved in THF (6 ml). Sodium hydride (40 mg) and 2-chloro-5-methoxy-pyrimidine (92 mg) were added and the mixture was heated to 75° C. for 46 h, then poured onto water, acidified with solid citric acid and the precipitate was filtered off. The crude material was purified by crystallization from methanol to give ethanesulfonic acid [6-[2-(5-methoxy-pyrimidin-2-yloxy)-ethoxy]-5-(2-methoxy-phenoxy)-[2,2']bipyrimidinyl-4-yl]-amide (61 mg) as a white powder. LC-MS: $t_R$: 3.87, [M–H]⁺: 554.02.

According to the procedures described in the Examples 1 to 12 and in the literature [5], [6], [7], [8] and [11] the compounds depicted in the following tables of Examples 13 to 16 can be prepared.

Example 13

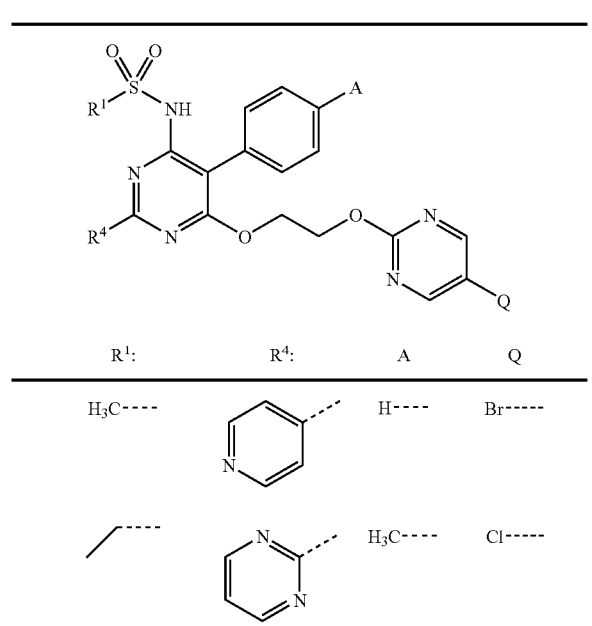

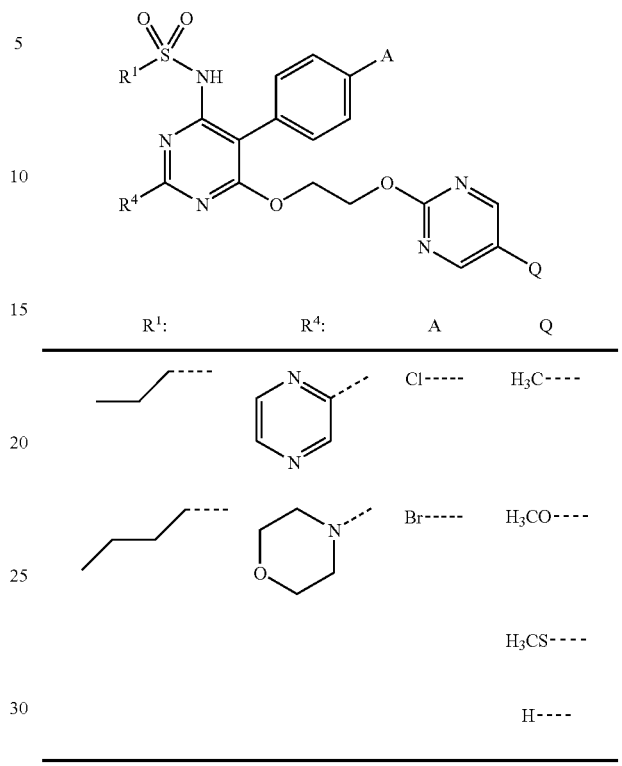

In the Examples 14 to 84 the retention time $t_R$ is given in minutes and the molecular mass is always given as [M+H]⁺ for the LC-MS analyses. Standard measurements were made on a Waters Micromass LC-MS system. For Example 57, a Finnigan Navigator LC-MS system was used (see page 31).

Examples 14-84

| Ex. Nr | R¹: | R⁴: | Q | LC-MS |
|---|---|---|---|---|
| 14 | H₃C---- | pyrimidin-2-yl | Br----- | $t_R$: 4.05 [M + H]⁺: 592.09 |
| 15 | H₃C---- | pyrimidin-2-yl | H₃CO---- | $t_R$: 4.11 [M + H]⁺: 542.21 |

-continued

| | | | | |
|---|---|---|---|---|
| 16 | H₃C---- | (pyrimidin-2-yl) | H₃CS---- | $t_R$: 4.34 [M + H]⁺: 558.20 |
| 17 | H₃C---- | H | Br---- | $t_R$: 4.29 [M + H]⁺: 514.09 |
| 18 | H₃C---- | H | H₃CO---- | $t_R$: 4.08 [M + H]⁺: 464.16 |
| 19 | H₃C---- | H | H₃CS---- | $t_R$: 4.43 [M + H]⁺: 480.07 |
| 20 | H₃C---- | H | H₃CO₂S---- | $t_R$: 3.83 [M + H]⁺: 512.00 |
| 25 | n-Pr---- | (pyrimidin-2-yl) | Br---- | $t_R$: 4.83 [M + H]⁺: 634.12 |
| 26 | n-Pr---- | (pyrimidin-2-yl) | H₃CO---- | $t_R$: 4.47 [M + H]⁺: 584.38 |
| 27 | n-Pr---- | (pyrimidin-2-yl) | H₃CS---- | $t_R$: 4.75 [M + H]⁺: 600.24 |
| 32 | i-Pr---- | H | Br---- | $t_R$: 4.69 [M + H]⁺: 541.99 |
| 33 | i-Pr---- | H | H₃CO---- | $t_R$: 4.52 [M + H]⁺: 492.11 |
| 34 | i-Pr---- | H | H₃CS---- | $t_R$: 4.86 [M + H]⁺: 508.12 |
| 35 | i-Pr---- | H | H₃CO₂S---- | $t_R$: 4.31 [M + H]⁺: 540.14 |

| | | | | |
|---|---|---|---|---|
| 21 | H₃C---- | H | Br---- | $t_R$: 4.70 [M + H]⁺: 548.03 |
| 22 | H₃C---- | H | H₃CO---- | $t_R$: 4.28 [M + H]⁺: 498.23 |
| 23 | H₃C---- | H | H₃CS---- | $t_R$: 4.62 [M + H]⁺: 514.17 |
| 24 | H₃C---- | H | H₃CO₂S---- | $t_R$: 4.06 [M + H]⁺: 546.27 |
| 36 | i-Pr---- | H | Br---- | $t_R$: 5.09 [M + H]⁺: 576.20 |

-continued
| | | | | |
|---|---|---|---|---|
| 37 |  | | H₃CO---- | $t_R$: 4.69 [M + H]⁺: 526.29 |
| 38 |  | | H₃CS---- | $t_R$: 5.01 [M + H]⁺: 542.23 |
| 39 | 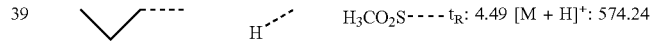 | | H₃CO₂S---- | $t_R$: 4.49 [M + H]⁺: 574.24 |
| 43 |  | | Br----- | $t_R$: 4.86 [M + H]⁺: 562.06 |
| 44 |  | | H₃CO---- | $t_R$: 4.45 [M + H]⁺: 512.21 |
| 45 |  | | H₃CS---- | $t_R$: 4.78 [M + H]⁺: 528.20 |
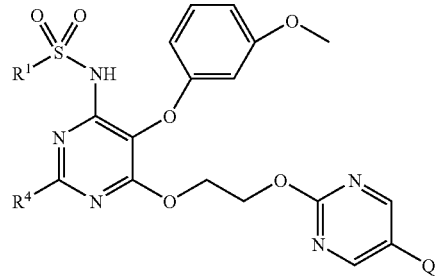
| | | | | |
|---|---|---|---|---|
| 28 |  | | Br----- | $t_R$: 5.17 [M + H]⁺: 554.14 |
| 29 |  | | H₃CO---- | $t_R$: 4.79 [M + H]⁺: 506.30 |
| 30 |  | | H₃CS---- | $t_R$: 5.11 [M + H]⁺: 522.27 |
| 31 |  | | H₃CO₂S---- | $t_R$: 4.54 [M + H]⁺: 554.43 |
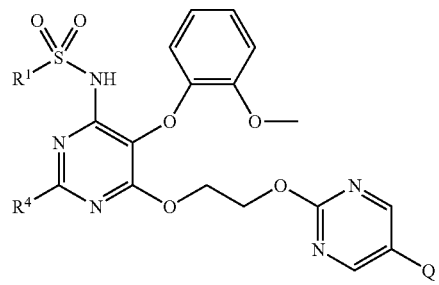
| | | | | |
|---|---|---|---|---|
| 40 |  | | Br----- | $t_R$: 4.59 [M + H]⁺: 527.11 |
| 41 |  | | H₃CO---- | $t_R$: 4.22 [M + H]⁺: 478.10 |
| 42 |  | | H₃CS---- | $t_R$: 4.61 [M + H]⁺: 494.17 |

-continued

| Ex. Nr | R¹: | R⁴: | A | Q | LC-MS |
|---|---|---|---|---|---|
| 50 | H₃C---- | H---- | H₃C---- | Br----- | $t_R$: 4.44 [M + H]⁺: 496.01 |
| 51 | H₃C---- | H---- | H₃C---- | H₃CO---- | $t_R$: 4.36 [M + H]⁺: 446.20 |
| 52 | H₃C---- | H---- | H₃C---- | H₃CS---- | $t_R$: 4.71 [M + H]⁺: 462.11 |

| Ex. Nr | R¹: | R⁴: | A | Q | LC-MS |
|---|---|---|---|---|---|
| 47 | H₃C---- | H---- | H₃C---- | Br----- | $t_R$: 4.42 [M + H]⁺: 481.95 |
| 48 | H₃C---- | H---- | H₃C---- | H₃CO---- | $t_R$: 4.21 [M + H]⁺: 432.17 |
| 49 | H₃C---- | H---- | H₃C---- | H₃CS---- | $t_R$: 4.59 [M + H]⁺: 448.14 |
| 53 | H₃C---- | H---- | Br----- | Br----- | $t_R$: 4.64 [M + H]⁺: 545.79 |
| 54 | H₃C---- | H---- | Br----- | H₃CO---- | $t_R$: 4.35 [M + H]⁺: 497.86 |
| 55 | H₃C---- | H---- | Br----- | H₃CS---- | $t_R$: 4.70 [M + H]⁺: 513.72 |
| 56 | H₃C---- | H---- | Br----- | H₃CO₂S---- | $t_R$: 4.16 [M + H]⁺: 545.93 |
| 57 | H₃C---- | H---- | Br----- | cyclopropyl---- | $t_R$: 1.07 [M + H]⁺: 507.94 |
| 58 | propyl---- | H---- | Br----- | Br----- | $t_R$: 4.91 [M + H]⁺: 559.80 |
| 59 | propyl---- | H---- | Br----- | H₃CO---- | $t_R$: 4.53 [M + H]⁺: 511.95 |
| 60 | propyl---- | H---- | Br----- | H₃CS---- | $t_R$: 4.87 [M + H]⁺: 527.92 |
| 61 | propyl---- | H---- | Br----- | H₃CO₂S---- | $t_R$: 4.31 [M + H]⁺: 559.86 |
| 62 | propyl---- | cyclopropyl---- | H₃C---- | Br----- | $t_R$: 5.65 [M + H]⁺: 534.14 |
| 63 | propyl---- | cyclopropyl---- | H₃C---- | H₃CO---- | $t_R$: 5.23 [M + H]⁺: 486.31 |

-continued

| | | | | | |
|---|---|---|---|---|---|
| 64 | /---- | ▽´--- | H₃C---- | H₃CS---- | t$_R$: 5.57 [M + H]$^+$: 502.34 |
| 65 | /---- | ▽´--- | H₃C---- | H₃CO₂S---- | t$_R$: 4.90 [M + H]$^+$: 534.44 |
| 66 | /---- | H´--- | Cl---- | Br---- | t$_R$: 4.93 [M + H]$^+$: 515.96 |
| 67 | /---- | H´--- | Cl---- | H₃CO---- | t$_R$: 4.48 [M + H]$^+$: 466.15 |
| 68 | /---- | H´--- | Cl---- | H₃CS---- | t$_R$: 4.85 [M + H]$^+$: 482.14 |
| 69 | /---- | H´--- | Cl---- | H₃CO₂S---- | t$_R$: 4.26 [M + H]$^+$: 514.21 |
| 70 | ∨---- | H´--- | Br---- | Br---- | t$_R$: 5.21 [M + H]$^+$: 573.86 |
| 71 | ∨---- | H´--- | Br---- | H₃CO---- | t$_R$: 4.80 [M + H]$^+$: 525.99 |
| 72 | ∨---- | H´--- | Br---- | H₃CS---- | t$_R$: 5.12 [M + H]$^+$: 541.92 |
| 73 | ∨---- | H´--- | Br---- | H₃CO₂S---- | t$_R$: 4.55 [M + H]$^+$: 573.97 |
| 74 | ∧∨---- | H´--- | H₃C---- | Br---- | t$_R$: 6.11 [M + H]$^+$: 524.06 |
| 75 | ∧∨---- | H´--- | H₃C---- | H₃CO---- | t$_R$: 4.94 [M + H]$^+$: 474.23 |
| 76 | ∧∨---- | H´--- | H₃C---- | H₃CS---- | t$_R$: 5.28 [M + H]$^+$: 490.31 |
| 77 | ∧∨---- | ▽´--- | H₃C---- | Br---- | t$_R$: 6.09 [M + H]$^+$: 564.18 |
| 78 | ∧∨---- | ▽´--- | H₃C---- | H₃CO---- | t$_R$: 5.69 [M + H]$^+$: 514.39 |
| 79 | ∧∨---- | ▽´--- | H₃C---- | H₃CS---- | t$_R$: 6.01 [M + H]$^+$: 530.34 |
| 80 | ∧∨---- | ▽´--- | H₃C---- | H₃CO₂S---- | t$_R$: 5.36 [M + H]$^+$: 562.30 |

-continued

| | | | | | |
|---|---|---|---|---|---|
| 81 | /\/ | H | Br | Br | $t_R$: 5.48 [M + H]$^+$: 588.13 |
| 82 | /\/ | H | Br | H$_3$CO | $t_R$: 5.06 [M + H]$^+$: 539.28 |
| 83 | /\/ | H | Br | H$_3$CS | $t_R$: 5.38 [M + H]$^+$: 556.11 |
| 84 | /\/ | H | Br | H$_3$CO$_2$S | $t_R$: 4.82 [M + H]$^+$: 587.41 |

Example 85

[Structure: sulfonamide-pyrimidine with R$^1$SO$_2$NH-, R$^4$, OR$^3$, and -O-CH$_2$CH$_2$-O-pyrimidine-Q]

| R$^1$: | R$^4$: | R$^3$: | Q |
|---|---|---|---|
| H$_3$C | 4-pyridyl | 2-methoxyphenyl | Br |
| ethyl | N-morpholinyl | 2-chloro-4-methoxyphenyl | Cl |
| n-butyl | 2-pyrazinyl | 3-methoxyphenyl | H$_3$C |
| n-pentyl | | | H$_3$CO |
| | | | H$_3$CS |
| | | | H |

Example 86

[Structure: sulfonamide-pyrimidine with R$^1$SO$_2$NH-, R$^4$, phenyl-A, and -O-CH$_2$CH$_2$CH$_2$-O-pyrimidine-Q]

| R$^1$: | R$^4$: | A | Q |
|---|---|---|---|
| H$_3$C | H | H | Br |
| n-propyl | H$_3$C | 4-pyridyl | Cl |
| cyclopropyl | 4-pyridyl | | H$_3$C |
| n-butyl | 2-pyrimidinyl | N-morpholinyl | Cl |
| | 2-pyrazinyl | | H$_3$C |
| n-pentyl | | Br | H$_3$CO |
| | | | H$_3$CS |
| | | | H |

Example 87

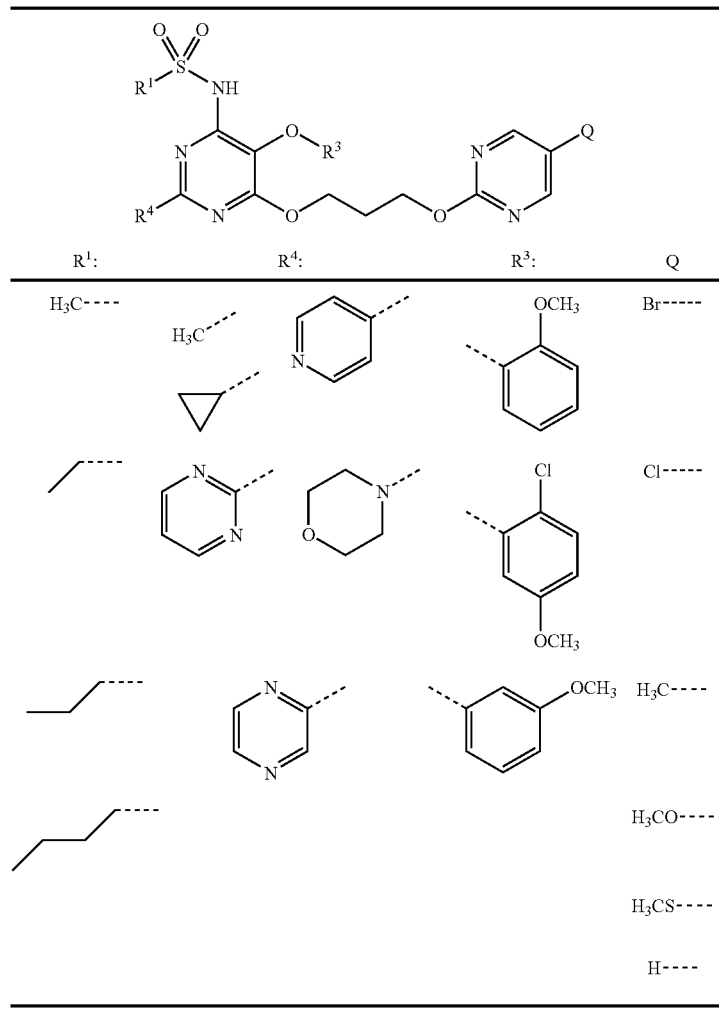

The invention claimed is:
1. A compound of the formula:

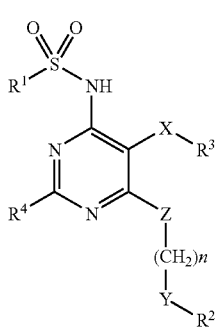

Formula I wherein
R¹ represents lower alkyl;
R² represents aryl; heteroaryl; lower alkyl;
R³ represents aryl; heteroaryl;
R⁴ represents hydrogen; trifluoromethyl; lower alkyl; lower alkyl-amino; lower alkoxy; lower alkoxy-lower alkyl; hydroxy-lower alkoxy; lower alkyl-sulfinyl; lower alkylthio; lower alkylthio-lower alkyl; hydroxy-lower alkyl; lower alkoxy-lower alkyl; hydroxy-lower alkoxy-lower alkyl; hydroxy-lower alkyl-amino; lower alkyl-amino-lower alkyl; amino; di-lower alkyl-amino; [N-(hydroxy-lower alkyl)-N-(lower alkyl)]-amino; aryl; aryl-amino; aryl-lower alkyl-amino; aryl-thio; aryl-lower alkyl-thio; aryloxy; aryl-lower alkoxy; aryl-lower alkyl; aryl-sulfinyl; heteroaryl; heteroaryl-oxy; heteroaryl-lower alkyl-oxy; heteroaryl-amino; heteroaryl-lower alkyl-amino; heteroaryl-thio; heteroaryl-lower alkyl-thio; heteroaryl-lower alkyl; heteroaryl-sulfinyl; heterocyclyl; heterocyclyl-lower alkoxy; heterocyclyl-oxy; heterocyclyl-amino; heterocyclyl-lower alkyl-amino; heterocyclyl-thio; heterocyclyl-lower alkyl-thio; heterocyclyl-lower alkyl; heterocyclyl-sulfinyl; cycloalkyl; cycloalkyl-oxy; cycloalkyl-lower alkoxy; cycloalkyl-amino; cycloalkyl-lower alkyl-amino; cycloalkyl-thio; cycloalkyl-lower alkyl-thio; cycloalkyl-lower alkyl; cycloalkyl-sulfinyl;

X represents oxygen; or a bond;

Y represents oxygen; —NH—; —NH—SO$_2$—; —NH—SO$_2$—NH—; —O—CO—NH—; —NH—CO—O—; or —NH—CO—NH—;

Z represents oxygen; sulfur; or —NH—;

n represents an integer selected from 2; 3; or 4;

or optically pure enantiomers or diastereomers, mixtures of enantiomers or diastereomers, diastereomeric racemates, mixtures of diastereomeric racemates or the meso-forms and pharmaceutically acceptable salts thereof.

2. The compound of claim 1 having the formula:

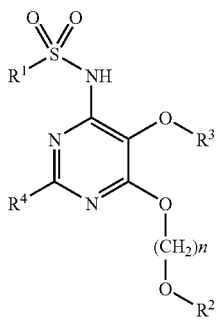

Formula II wherein

R$^1$ represents ethyl; propyl; iso-propyl; or butyl;

R$^2$ represents aryl; or heteroaryl;

and R$^3$, R$^4$ and n are as above or optically pure enantiomers or diastereomers, mixtures of enantiomers or diastereomers, diastereomeric racemates, mixtures of diastereomeric racemates and the meso-forms or pharmaceutically acceptable salts thereof.

3. The compound of claim 2 having the formula:

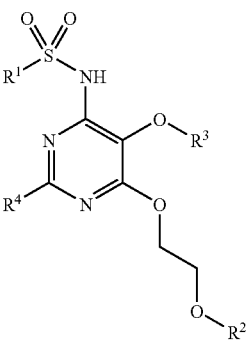

Formula III wherein

R$^1$ represents ethyl; propyl; or butyl;

R$^2$ represents aryl; or heteroaryl;

R$^4$ hydrogen; or heteroaryl;

and R$^3$ is as above or optically pure enantiomers or diastereomers, mixtures of enantiomers or diastereomers, diastereomeric racemates, mixtures of diastereomeric racemates or the meso-forms and pharmaceutically acceptable salts thereof.

4. The compound of claim 3 having the formula:

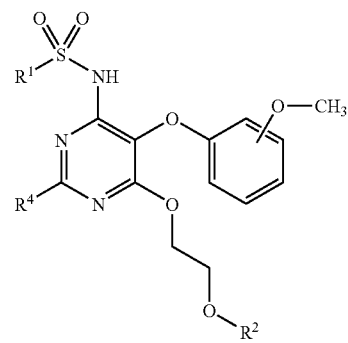

Formula IV wherein

R$^1$ represents ethyl; propyl; iso-propyl; or butyl;

R$^2$ represents aryl; or heteroaryl

R$^4$ hydrogen; or heteroaryl;

or optically pure enantiomers or diastereomers, mixtures of enantiomers or diastereomers, diastereomeric racemates, mixtures of diastereomeric racemates and the meso-forms or pharmaceutically acceptable salts thereof.

5. The compound of claim 1 having the formula:

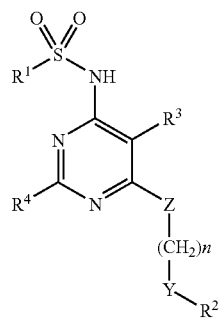

Formula V wherein

R$^1$, R$^2$, R$^3$ and R$^4$ as well as Y, Z and n are as above or optically pure enantiomers or diastereomers, mixtures of enantiomers or diastereomers, diastereomeric racemates, mixtures of diastereomeric racemates and the meso-forms or pharmaceutically acceptable salts thereof.

6. The compound of claim 5 having the formula:

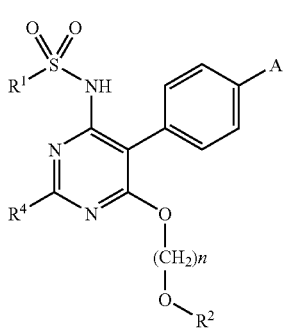

Formula VI wherein
R¹ represents ethyl; propyl; or butyl;
R² represents aryl; or heteroaryl;
R⁴ represents hydrogen or heteroaryl;
A represents hydrogen; methyl; ethyl; chlorine; or bromine;
and n represents the integers 2; or 3;
or optically pure enantiomers or diastereomers, mixtures of enantiomers or diastereomers, diastereomeric racemates, mixtures of diastereomeric racemates and the meso-forms or pharmaceutically acceptable salts thereof.

7. The compound of claim 6 having the formula:

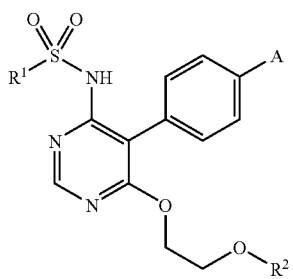

Formula VII wherein
R¹ represents ethyl; propyl; or butyl;
R² represents heteroaryl;
A represents methyl; chlorine; or bromine;
or optically pure enantiomers or diastereomers, mixtures of enantiomers or diastereomers, diastereomeric racemates, mixtures of diastereomeric racemates or the meso-forms and pharmaceutically acceptable salts thereof.

8. The compound of claim 1 selected from the group consisting of
Ethanesulfonic acid {6-[2-(5-bromo-pyrimidin-2-yloxy)-ethoxy]-5-p-tolyl-pyrimidin-4-yl}-amide;
n-Propanesulfonic acid {6-[2-(5-bromo-pyrimidin-2-yloxy)-ethoxy]5-p-tolyl-pyrimidin-4-yl}-amide;
Ethanesulfonic acid [6-[2-(5-bromo-pyrimidin-2-yloxy)-ethoxy]-5-(4-chloro-phenyl)-pyrimidin-4-yl]-amide;
n-Propanesulfonic acid [6-[2-(5-bromo-pyrimidin-2-yloxy)-ethoxy]-5-(4-chloro-phenyl)-pyrimidin-4-yl]-amide;
Ethanesulfonic acid {5-(4-bromo-phenyl)-6-[2-(5-bromo-pyrimidin-2-yloxy)-ethoxy]-pyrimidin-4-yl}-amide;
n-Propanesulfonic acid {5-(4-bromo-phenyl)-6-[2-(5-bromo-pyrimidin-2-yloxy)-ethoxy]-pyrimidin-4-yl}-amide;
Ethanesulfonic acid [6-[2-(5-bromo-pyrimidin-2-yloxy)-ethoxy]-5-(2-methoxy-phenoxy)-[2,2']bipyrimidinyl-4-yl]-amide;
n-Propanesultonic acid [6-[2-(5-bromo-pyrimidin-2-yloxy)-ethoxy]-5-(2-methoxy-phenoxy)-[2,2']bipyrimidinyl-4-yl]-amide;
Ethanesulfonic acid [6-[2-(5-bromo-pyrimidin-2-yloxy)-ethoxy]-5-(2-methoxy-phenoxy)-pyrimidin-4-yl]-amide;
n-Propanesulfonic acid [6-[2-(5-bromo-pyrimidin-2-yloxy)-ethoxy]-5-(2-methoxy-phenoxy)-pyrimidin-4-yl]-amide;
N-[6-[2-(5-Bromo-pyrimidin-2-yloxy)-ethoxy]-5-p-tolyl-pyrimidin-4-yl]methanesulfonamide;
Ethanesulfonic acid [5-(2-chloro-5-methoxy-phenoxy)-6-[2-(5-methylSulfanyl-pyrimidin-2-yloxy)-ethoxy]-pyrimidin-4-yl]-amide;
Butane-1-sulfonic acid [5-(3-methoxy-phenoxy)-6-[2-(5-methylsulfanyl-pyrimidin-2-yloxy)-ethoxy]-pyrimidin-4-yl]-amide;
Ethanesulfonic acid [5-(4-bromo-phenyl)-6-[2-(5-methylsultanyl-pyrimidin-2-yloxy)-ethoxy]-pyrimidin-4-yl]-amide;
Propane-1-sulfonic acid [5-(2-chloro-5-methoxy-phenoxy)-6-[2-(5-methylsulfaflyl-pyrimidin-2-yloxy)-ethoxy]-pyrimidin-4-yl]-amide;
or pharmaceutically acceptable salts thereof.

9. The compound of claim 1 selected from the group consisting of:
N-[5-(4-Bromo-phenyl)-6-[2-(5-bromo-pyrimidin-2-yloxy)-ethoxy]-pyrimidin-4-yl]-methanesulfonamide;
Ethanesulfonic acid [5-(4-bromo-phenyl)-6-[2-(5-bromo-pyrimidin-2-yloxy)-ethoxy]-pyrimidin-4-yl]-amide;
Propane-1-sulfonic acid [5-(4-bromo-phenyl)-6-[2-(5-bromo-pyrimidin-2-yloxy)-ethoxy]-pyrimidin-4-yl]-amide;
Propane-1-sulfonic acid [6-[2-(5-bromo-pyrimidin-2-yloxy)-ethoxyl]-5-(2-methoxy-phenoxy)-pyrimidin-4-yl]-amide;
Ethanesulfonic acid [6-[2-(5-methylsulfanyl-pyrimidin-2-yloxy)-ethoxy]-5-p-tolyl-pyrimidin-4-yl]-amide;
Propane-1-sulfonic acid [5-(4-bromo-phenyl)-6-[2-(5-methylsulfanyl-pyrimidin-2-yloxy)-ethoxy]-pyrimidin-4-yl]-amide;
Ethanesulfonic acid [6-[2-(5-bromo-pyrimidin-2-yloxy)-ethoxyl]-5-(2-chloro-5-methoxy-phenoxy)-pyrimidin-4-yl]-amide;
Propane-1-sulfonic acid [6-[2-(5-bromo-pyrimidin-2-yloxy)-ethoxy]-5-(2-chloro-5-methoxy-phenoxy)-pyrimidin-4-yl]-amide;
or pharmaceutically acceptable salts thereof.

* * * * *